United States Patent
Lansing

(10) Patent No.: US 10,119,968 B2
(45) Date of Patent: Nov. 6, 2018

(54) SELF-CONTAINED DIAGNOSTIC TEST WITH ADVANCEABLE TEST STRIP

(71) Applicant: TEST ANYWHERE TECHNOLOGY, Mt. Pleasant, SC (US)

(72) Inventor: Bliss Hanlon Lansing, Ellicott City, MD (US)

(73) Assignee: TEST ANYWHERE TECHNOLOGY, Mt. Pleasant, SC (US)

( * ) Notice: Subject to any disclaimer, the term of this patent is extended or adjusted under 35 U.S.C. 154(b) by 797 days.

(21) Appl. No.: 13/907,373

(22) Filed: May 31, 2013

(65) Prior Publication Data

US 2014/0072960 A1     Mar. 13, 2014

Related U.S. Application Data

(60) Provisional application No. 61/654,869, filed on Jun. 2, 2012.

(51) Int. Cl.
| | | |
|---|---|---|
| *G01N 33/571* | (2006.01) | |
| *G01N 33/53* | (2006.01) | |
| *G01N 1/02* | (2006.01) | |

(52) U.S. Cl.
CPC ....... *G01N 33/571* (2013.01); *G01N 33/5302* (2013.01); *G01N 33/5304* (2013.01); *G01N 2001/028* (2013.01)

(58) Field of Classification Search
CPC ........... G01N 33/5302; G01N 33/5304; G01N 2001/028
See application file for complete search history.

(56) References Cited

U.S. PATENT DOCUMENTS

| 3,163,160 A | 12/1964 | Cohen |
| 3,450,129 A | 6/1969 | Avery et al. |

(Continued)

FOREIGN PATENT DOCUMENTS

| EP | 1024354 A1 | 8/2000 |
| EP | 0861330 B1 | 8/2003 |

(Continued)

OTHER PUBLICATIONS

International search report and written opinion dated Aug. 21, 2013 for PCT/US2013/043734.

*Primary Examiner* — Scott Long
*Assistant Examiner* — Gary E Hollinden
(74) *Attorney, Agent, or Firm* — Kunzler, PC

(57) ABSTRACT

A test unit collects and analyzes biological specimens on-site. It has one or more openings that allow reagent capsules to be inserted and guided into a testing chamber. Reagent capsules are pre-loaded with chemicals for screening and are configured as blister packs. A button mechanism allows projection(s) to open the blister packs to allow chemicals within the capsules to mix inside the testing chamber. A medical swab is affixed to a pop top dispenser cap and can be pressed to allow the swab to be inserted into the mixed chemicals. A visible test strip mount attached to the testing chamber has a lever to manipulate a test strip in and out of the testing chamber. This test strip may be slid through a uni-directional seal on a capsule and into a chemical for testing. The test strip will test for the presence of an infectious disease.

21 Claims, 32 Drawing Sheets

(56) References Cited

U.S. PATENT DOCUMENTS

| | | | |
|---|---|---|---|
| 3,776,220 A | 12/1973 | Monaghan | |
| 3,890,954 A | 6/1975 | Greenspan | |
| 3,923,604 A | 12/1975 | Monaghan | |
| 3,954,564 A | 5/1976 | Mennen | |
| 3,966,552 A | 6/1976 | Pagano et al. | |
| 4,014,746 A | 3/1977 | Greenspan | |
| 4,014,748 A | 3/1977 | Spinner et al. | |
| 4,184,483 A | 1/1980 | Greenspan | |
| 4,196,167 A | 4/1980 | Olsen | |
| 4,206,843 A | 6/1980 | Rainey | |
| 4,223,093 A | 9/1980 | Newman et al. | |
| 4,252,904 A | 2/1981 | Nelson et al. | |
| 4,311,792 A | 1/1982 | Avery | |
| 4,312,950 A | 1/1982 | Syder et al. | |
| 4,353,868 A | 10/1982 | Joslin et al. | |
| 4,355,113 A | 10/1982 | Mennen | |
| 4,387,725 A | 6/1983 | Mull | |
| 4,409,988 A | 11/1983 | Greenspan | |
| 4,562,043 A | 12/1985 | Mennen et al. | |
| 4,749,655 A | 6/1988 | Monthoney et al. | |
| 4,770,853 A | 9/1988 | Bernstein | |
| 5,169,789 A * | 12/1992 | Bernstein | G01N 33/5302 422/413 |
| 5,238,649 A | 8/1993 | Nason | |
| 5,250,412 A | 10/1993 | Giegel | |
| 5,266,266 A | 11/1993 | Nason | |
| 5,611,995 A | 3/1997 | De Zoeten et al. | |
| 5,827,675 A | 10/1998 | Skiffington et al. | |
| 5,869,003 A | 2/1999 | Nason | |
| 5,879,635 A | 3/1999 | Nason | |
| 5,965,453 A | 10/1999 | Skiffington et al. | |
| 6,180,395 B1 | 1/2001 | Skiffington et al. | |
| 6,248,294 B1 | 6/2001 | Nason | |
| 6,423,550 B1 | 7/2002 | Jenkins et al. | |
| 6,524,530 B1 | 2/2003 | Igarashi et al. | |
| 6,991,898 B2 | 1/2006 | O'Connor | |
| 7,060,505 B2 * | 6/2006 | Guirguis | A61B 5/117 422/402 |
| 7,098,040 B2 | 8/2006 | Kaylor et al. | |
| 7,863,053 B2 | 1/2011 | Lyng et al. | |
| 7,932,099 B2 * | 4/2011 | Egan | B01L 3/5023 435/287.1 |
| 8,038,965 B2 | 10/2011 | Keren | |
| 2005/0131314 A1 | 6/2005 | Hird et al. | |
| 2006/0040405 A1 | 2/2006 | Charlton et al. | |
| 2006/0051237 A1 * | 3/2006 | Wang | B01L 3/5023 422/417 |
| 2008/0260581 A1 | 10/2008 | Rosman et al. | |
| 2008/0299648 A1 | 12/2008 | Tomer | |
| 2009/0197283 A1 * | 8/2009 | Gold | B01L 3/5029 435/7.9 |
| 2011/0097820 A1 | 4/2011 | Lyng et al. | |
| 2011/0236879 A1 | 9/2011 | Egan et al. | |
| 2011/0256531 A1 | 10/2011 | Rajagopal et al. | |
| 2012/0082598 A1 * | 4/2012 | Baydoun | G01N 33/558 422/423 |
| 2012/0082977 A1 | 4/2012 | Rajagopal et al. | |

FOREIGN PATENT DOCUMENTS

| | | |
|---|---|---|
| EP | 1338338 A1 | 8/2003 |
| EP | 1697717 A1 | 9/2006 |
| EP | 1714133 A1 | 10/2006 |
| EP | 0981729 B1 | 4/2007 |
| WO | WO 2005/068969 A1 | 7/2005 |
| WO | WO 2005/071388 A1 | 8/2005 |
| WO | WO 2010/129726 A1 | 11/2010 |

\* cited by examiner

SELF-CONTAINED DIAGNOSTIC TEST WITH ADVANCEABLE TEST STRIP

CROSS-REFERENCE

This application claims the benefit of U.S. Provisional Application No. 61/654,869, entitled "Self Diagnostic Test" and filed Jun. 2, 2012, which is incorporated herein by reference.

BACKGROUND OF THE INVENTION

1. Field of Invention

This disclosure relates to medical devices and kits used for diagnostic and screening purposes. More specifically, the disclosure relates to an improved and fully self-contained test unit designed for use in a non-hospital or non-clinic setting to detect bacteria, viruses, or other pathogens, such as strep throat-causing bacteria.

2. Description of Related Art

Medical swabs are often utilized to collect biological specimens for further analysis. Medical swabs can be comprised of an elongated shaft with a fibrous (foam or cotton) tip, or a serrated metal tip to collect culture samples from various areas of infection in question, including the ear, nose, or throat. Sample specimens may interact with chemical reagents to indicate the presence of infection. Commonly, tests performed include enzymatic tests, monoclonal-based tests, fluorescent tests, agglutination tests, and other tests that provide information regarding a tester's condition or presence of bacteria.

Conventional specimen collection often requires that the biological specimen be transferred or transported from a swab to a slide, test tube, or other medical apparatus for contact with chemical reagents. Such transportation of the biological specimens poses risks to the accuracy of test results and analysis. This is because there is often an insufficient amount of the biological sample transferred from the test swab to a slide or test tube. Moreover, during transportation there is the potential that the biological specimen may become contaminated due to multiple people handling the biological sample or from contact with various unsterile surfaces. Further, if the biological sample is not transferred and analyzed in a timely manner, the biological sample may become invalid or dry, thus decreasing the reliability of the test.

Many diagnostic tests may also require special equipment or need to be performed by medical professionals. This can increase the cost and burden on the tester and may reduce the likelihood of early detection.

Needs therefore exist for improved diagnostic tests, and particularly for detection products designed and sold for non-hospital and non-clinic setting such as grocery stores, drug stores, pharmacies, and the home.

3. References of Interest

The following references may be of interest: U.S. Pat. Nos. 8,038,965, 7,098,040, 6,524,530, 6,248,294, 6,180,395, 5,965,453, 5,879,635, 5,869,003, 5,827,675; U.S. Publication No. 2008/0260581, 2012/0082977; PCT Publication No. WO2010/129726; European Patent Publication No. EP1714133A1, EP1697717A1, EP1338338A1, EP1024354A1, EP0981729B1, EP0861330B1.

SUMMARY OF THE INVENTION

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description. In certain embodiments, the disclosed embodiments may include one or more of the features described herein.

Advances in technology, coupled with consumer demand have redefined trends in the health industry and pushed the market towards developing convenient health care products that do not require a visit to a hospital or clinic. For example, in the past if a woman thought she was pregnant, the woman would have to visit a doctor to have a pregnancy test performed. Now, however, a woman has the ability to take an at home pregnancy test and administer the test herself. In another example, a subject who is interested in taking measurements of him or herself such as weight, height, and body mass index can use a diagnostic machine found in drug stores, pharmacies, and groceries stores instead of needing to visit a hospital or clinic. The shift from patients to consumers who can take charge of their own health has made non-hospital and non-clinic testing a growing multi-billion dollar industry worldwide. Drugstores are carrying or administering an increased number of medical tests that can be performed in non-hospital and non-clinic settings because people desire the financial savings, convenience, privacy, and other benefits that arise from managing their health care at more convenient locations.

In order to minimize and/or reduce risks that may produce invalid tests and thus increasing test reliability and accessibility, a fully self-contained screening test is disclosed herein. The self-contained test unit can enhance contact between a specimen and reagents by reducing the amount of time it takes to perform the test and the number of people handling the sample. The risk of contamination by direct contact can be minimal as the compact, self-contained design can essentially eliminate the transportation of the specimen across unsterile environments. Additionally, the test can be designed so that a single tester can immediately perform the analysis on site, without delay. This efficiency helps preserves the specimen and ensures greater test reliability.

Example embodiments herein provide for a test that is safe to use, and is fully self-contained, having no or reduced risk of contamination and little risk for spills or exposure of chemicals to the tester. Unlike many existing designs, the testing unit may not expose a tester to any chemical agents disposed within the testing kit. This can be because all of the reagents within the testing kit may be in a closed chamber until the swab is sealed into the container. Therefore, there may be little to no risk of exposure to chemical agents or bodily fluids. Once the sample is obtained, the self-contained testing unit may lock, and the fluids and chemical components may be maintained in the testing chamber.

Embodiments herein disclose an aesthetically appealing, easy-to-use screening test that can be configured to analyze and/or detect types of bacteria such as streptococcal group A. The testing device can provide for minimal risk of contamination or testing error because the device can be designed to operate in a series of sequential steps to ensure optimal testing accuracy. Example embodiments can utilize a pre-loaded and divided chamber that can allow for a test sample to be exposed to reagents at a desired time. After the sample is exposed to the reagents, a reading may be taken and analyzed. In other words, to reduce test contamination, the test may feature a sequential progression of test components and stages that can limit and/or reduce errors by a tester. Specifically, the internal controls built into the design by way of compartments and divided chambers can increase the safety and simplicity of the test. These features can ensure the test is designed in a consumer friendly manner, where any person of appropriate age or of minimal professional training may use the testing kit at home, drug stores, pharmacies, or any other desired location.

Example embodiments disclosed herein describe methods and systems utilizing a self-contained screening test. The test may include a testing chamber having a track disposed on an inner surface of the testing chamber, the track being configured for reagent capsules to be individually loaded into the testing chamber. The test may include reagent capsules that have been pre-loaded with chemicals. All capsules can be loaded into the base of the test tube via a sliding track. The capsules can be designed with breakaway dividers. Specifically, the ceiling and floor of each capsule may break away by way of a compression button. In some embodiments, only the last reagent capsule to be loaded contains a permanent base. The ceiling of the base capsule can open to receive the other reagents. However, the bottom of the capsule can remain intact to hold the chemicals in place.

Accordingly, embodiments describe a simple, compact, and easy-to-use testing device wherein all the components within the testing device may be isolated to ensure sanitized/clean components. The test may also include a movable test strip container unit configured to house a test strip. The test strip may be held in an independent chamber affixed to the test tube. Therefore, there may be little to no risk of contamination by manual handling of the test strip or premature exposure to the specimen or chemical reagents because the test strip may not be housed within the test tube. The test strip may be mobile by way of a lever. The lever can move the test strip through a uni-directional rubber seal (built into a reagent capsule) into the chemical mixture without exposing the test strip to the outside environment. A button may be positioned at the base of the testing chamber, wherein if the button is pressed, a projection will break the dividers on the reagent capsules to allow the chemicals to mix and open to the test tube. Accordingly, the swab may be disposed into the chemical mixture without touching any surface within the testing chamber. This can ensure that a sufficient amount of the sample fluid is retained for testing, as there may be little to no risk of the specimen being wiped from the swab as there is if the swab has to break through a seal.

Example embodiments can offer a benefit of convenient testing, and may be conveniently packaged and easy to administer or perform. Individuals may be reliably screened and/or tested for the presence of bacteria in convenient locations in a timely fashion, thus avoiding the added cost and inconvenience of a visit to a physician's office.

A new screening test apparatus can include a testing chamber having an opening and two or more capsules in the testing chamber that contain chemicals and have first breakaway dividers separating the capsules from each other. The capsules may be configured to be manipulated to open the breakaway dividers and allow the chemicals in the capsules to mix, and the testing chamber may be configured for a testing sample to pass through the opening, and to be inserted into the capsules once the breakaway dividers have been opened.

One or more of the capsules may have a second breakaway divider separating the interiors of the one or more of the capsules from the interior of the testing chamber, where the one or more of the capsules may be configured to be manipulated to open the second breakaway divider and expose the chemicals in the capsules to the interior of the testing chamber. The testing chamber may include a pop-top configured to attach to the testing sample and to be depressed to insert the testing sample into the capsules. The pop-top may be attached to a removable cap that closes the opening. The pop-top may have surface ridges for easy gripping. The pop-top may be configured to lock the cap in place on the testing chamber when depressed.

The screening test apparatus may also include a timer and alarm attached to the testing chamber to indicate when a test strip is to be inserted into a mixture of chemicals or when the test strip is to be read. The testing chamber further may also include a track disposed on an inner surface and configured for capsules to be loaded into the testing chamber. The track may have stop locks configured to hold a capsule in place once it has been loaded. The track may have projections configured to prevent movement of capsules past the projections and further into the testing chamber and depressions configured to mate with projections in the capsules to secure them in place and prevent their movement after insertion.

The screening test apparatus may also include a button having one or more projections, where the button can be configured so that pressing the button can push the projections against the breakaway dividers and opens them. One or more of the capsules may have a seal entry configured to allow entry of an object into the interior of the one or more capsules without allowing the chemicals contained in the one or more capsules to flow through the seal entry around the object. The screening test apparatus may also include a test strip insertion mechanism attached to but outside of the testing chamber and configured to insert a test strip into the testing chamber and expose the test strip to an analyte.

The test strip insertion mechanism may include a test strip cover configured to prevent the test strip from being directly touched by a solid surface other than the test strip cover as it is inserted into the testing chamber. The test strip insertion mechanism may include a sliding tab configured to be manipulated to insert the test strip into the testing chamber or to remove the test strip from the testing chamber. The testing chamber may be configured so that when the testing sample is inserted into the capsules it does not contact any solid surface. The screening test apparatus may also include a tongue depressor removably attached to the testing chamber.

A new capsule can be configured for insertion into the track of the screening test apparatus disclosed above and may have a breakaway divider configured to open upon application of pressure. The capsule may also include a uni-directional seal entry.

A new screening test apparatus may include a testing chamber having an opening configured for insertion of one or more capsules containing chemicals, stop locks on an interior surface of the testing chamber configured to secure the capsules upon their insertion into the testing chamber, and an opening mechanism configured to expose the contents of one or more of the secured capsules to an interior of the testing chamber, where the testing chamber may be configured for insertion of a testing sample into the exposed contents of the one or more secured capsules.

In a new screening test method, pressure can be exerted on one or more capsules, rupturing the capsules and mixing contents of the capsules or exposing the contents to the interior of a testing chamber, a test sample insertion mechanism on the testing chamber can be depressed to insert a testing sample into the contents of the capsules, and a test strip insertion mechanism can be slid to insert a test strip into the contents of the capsules. Rupturing the capsules may mix the contents of the capsules and expose the contents to the interior of the testing chamber. A testing sample may be retrieved with a testing sample retrieving device attached to the testing sample insertion mechanism. Inserting a test strip into the contents of the capsules may include inserting the test strip through a seal entry in the side of one of the one or more capsules.

An aspect of the disclosure provides a device for determining the presence of an analyte is provided. The device comprises a testing chamber having an open portion and a reagent portion, an articulable element coupled to the testing chamber, a cover removably coupled to the open portion of the testing chamber, and a test strip. The testing chamber comprises an open portion at or near a first end and a reagent portion at or near the second end opposite the first end. The open portion will typically be hollow. The articulable element is coupled to the testing chamber. The articulable element can be articulated to cause a plurality of reagents held by the reagent portion of the testing chamber to mix. The cover is configured for advancing a specimen into the reagent portion of the testing chamber. The test strip is coupled to the testing chamber and is configured to be advanced into the reagent portion of the testing chamber to determine the presence of an analyte in a mixture of the plurality of reagents and the specimen.

The reagent portion of the testing chamber may comprise a first reagent storage element and a second reagent storage element. The first reagent storage element may comprise a first reagent. The second reagent storage element may comprise a second reagent. For example, to test for strep A, the first reagent may comprise one or more of an extraction reagent, 2M or 4M sodium nitrate, non-viable group A streptococci, and 0.1% sodium azide, and the second reagent may comprise one or more of an extraction reagent, 0.2-0.3M acetic acid, non-viable group C streptococci, and 0.1% sodium azide. The first reagent storage element may comprise a first blister pack. The second reagent storage element may comprise a second blister pack. Articulating the articulable element comprises breaking one or more of the first blister pack and the second blister pack. The articulable element may comprise one or more projections for tearing or breaking one or more of the first blister pack and the second blister pack. One or more of the first reagent storage element and the second reagent storage element may be removable from the reagent portion and may be interchangeable.

The removable partition may comprise a retractable seal. The articulable element may comprise a pressable button. The device may further comprise an elongate specimen collection element having a first end for coupling the elongate element to the cover and a second end opposite the first end for carrying the specimen. The cover may comprise a depressible button configured to be pressed to advance the second end of the elongate element including the specimen into the reagent portion of the testing chamber. The device may further comprise a sliding mechanism coupled to the testing chamber and the test strip. The sliding mechanism may be configured to be actuated to advance the test strip into the reagent portion of the testing chamber. The test strip may be configured to detect the presence of an infectious disease such as one or more of strep throat, influenza, whooping cough, a sexually transmitted disease, Chlamydia, and Gonorrhea. For example, to test for strep A, the test strip may comprise first line having an immobilized strep A antibody and a second line for ensuring that the reagents have properly mixed.

Another aspect of the disclosure provides a method for determining the presence of an analyte is provided. A first reagent is mixed with a second reagent in a reagent portion of a testing chamber. For example, to test for strep A, the first reagent may comprise one or more of an extraction reagent, 2M or 4M sodium nitrate, non-viable group A streptococci, and 0.1% sodium azide, and the second reagent may comprise one or more of an extraction reagent, 0.2-0.3M acetic acid, non-viable group C streptococci, and 0.1% sodium azide. A specimen collection element carrying a specimen thereon is advanced into the reagent portion of the testing chamber. The test strip is advanced into the reagent portion of the testing chamber. The test strip is observed to determine the presence of the analyte in a mixed sample comprising the first reagent, the second reagent, and the sample. For example, to test for strep A, the test strip may comprise first line having an immobilized strep A antibody and a second line for ensuring that the reagents have properly mixed.

The first reagent may be mixed with the second reagent by articulating an articulable element coupled to the testing chamber to open a first reagent storage element and a second reagent storage element to one another.

The specimen collection element may be advanced by pressing a button of a cover coupled to the testing chamber and the specimen collection element.

The test strip may be advanced into the reagent portion of the testing chamber by sliding a sliding mechanism coupled to the testing chamber and test strip.

The test strip can be observed to determine the presence of the analyte in the mixed sample to determine the presence of a disease. The disease may be an infectious disease such as one or more of strep throat, influenza, whooping cough, a sexually transmitted disease, Chlamydia, and Gonorrhea.

Yet another aspect of the disclosure provides a self-contained device for detecting a disease. The self-contained device comprises an elongate specimen collection element, an elongate testing chamber, a cap, an articulable element, and a sliding mechanism. The elongate specimen collection element has a first end and a second end for collecting and carrying a biological specimen. The elongate testing chamber comprises an open portion at or near a first end and a reagent mixing portion at or near the second end. The reagent mixing portion is configured to carry a first capsule containing a first reagent and a second capsule containing a second reagent. The cap is configured to be coupled to the open portion of the elongate testing chamber and to the first end of the elongate specimen collection element. The cap is configured to position at least the second end of the elongate specimen collection element in the open portion of the elongate testing chamber when coupled thereto. The cap comprises a pressable element configured to be pressed to advance at least the second end of the elongate specimen collection element into the reagent mixing portion. The articulable element is coupled to the elongate testing chamber and is configured to be articulated to open the first reagent capsule and the second reagent capsule to one another. The sliding mechanism is coupled to the testing chamber and configured to be slid to advance a test strip into the reagent portion of the testing chamber.

Yet another aspect of the disclosure provides a screening test. The screening test comprises a testing chamber comprising an opening and two or more capsules in the testing chamber. The two or more capsules in the testing chamber contain chemicals and comprise first breakaway dividers separating the capsules from each other. The capsules are configured to be manipulated to open the breakaway dividers and allow the chemicals in the capsules to mix. The testing chamber is configured for a testing sample to pass through the opening and to be inserted into the capsules once the breakaway dividers have been opened.

One or more of the capsules may comprise a second breakaway divider separating the interiors of the one or more of the capsules from the interior of the testing chamber. The one or more of the capsules may be configured to be manipulated to open the second breakaway divider and expose the chemicals in the capsules to the interior of the testing chamber.

The testing chamber may further comprise a pop-top configured to attach to the testing sample and to be depressed to insert the testing sample into the capsules. The pop-top may be attached to a removable cap that closes the opening. The pop-top may comprise surface ridges for easy gripping. The pop-top may be configured to lock the cap in place on the testing chamber when depressed.

The screening test apparatus may further comprise a timer and alarm attached to the testing chamber to indicate when a test strip is to be inserted into a mixture of chemicals or when the test strip is to be read.

The testing chamber of the screening test apparatus may further comprise a track disposed on an inner surface and configured for capsules to be loaded into the testing chamber. The track may comprise stop locks configured to hold a capsule in place once it has been loaded. The track may comprise projections configured to prevent movement of capsules past the projections and further into the testing chamber and depressions configured to mate with projections in the capsules to secure them in place and prevent their movement after insertion. A capsule configured for insertion into the track may be provided. This capsule may comprise a breakaway divider configured to open upon application of pressure. This capsule may also comprise a uni-directional seal entry.

The screening test apparatus may further comprise a button comprising one or more projections. The button may be configured so that pressing the button pushes the projections against the breakaway dividers and opens them.

One or more of the capsules may comprise a seal entry configured to allow entry of an object into the interior of the one or more capsules without allowing the chemicals contained in the one or more capsules to flow through the seal entry around the object.

The screening test apparatus may further comprise a test strip insertion mechanism attached to but outside of the testing chamber and configured to insert a test strip into the testing chamber and expose the test strip to an analyte. The screening test apparatus may further comprise a test strip insertion mechanism attached to the testing chamber and configured to insert a test strip into the testing chamber through the seal entry and expose the test strip to an analyte. The test strip insertion mechanism may comprise a test strip cover configured to prevent the test strip from being directly touched by a solid surface other than the test strip cover as it is inserted into the testing chamber. The test strip insertion mechanism may comprise a sliding tab configured to be manipulated to insert the test strip into the testing chamber or to remove the test strip from the testing chamber.

The testing chamber of the screening test apparatus may be configured so that when the testing sample is inserted into the capsules it does not contact any solid surface.

The screening test apparatus of may further comprise a tongue depressor removably attached to the testing chamber.

Yet another aspect of the disclosure provides a screening test apparatus. The screening test apparatus comprises a testing chamber, stop locks on an interior surface of the testing chamber, and an opening mechanism. The testing chamber comprises an opening configured for insertion of one or more capsules containing chemicals. The stop locks are configured to secure the capsules upon their insertion into the testing chamber. The opening mechanism is configured to expose the contents of one or more of the secured capsules to an interior of the testing chamber. The testing chamber is configured for insertion of a testing sample into the exposed contents of the one or more secured capsules.

Yet another aspect of the disclosure provides a screening test method. Pressure is exerted on one or more capsules, rupturing the capsules and mixing contents of the capsules or exposing the contents to the interior of a testing chamber. A test sample insertion mechanism on the testing chamber is depressed to insert a testing sample into the contents of the capsules. A test strip insertion mechanism is slid to insert a test strip into the contents of the capsules. Rupturing the capsules can mix the contents of the capsules and expose the contents to the interior of the testing chamber. A testing sample may be retrieved with a testing sample retrieval device attached to the testing sample insertion mechanism. A test strip may be inserted into the contents of the capsules by inserting the test strip through a seal entry in the side of one of the one or more capsules.

Yet another aspect of the disclosure provides a device. The device comprises: (a) an elongated tube comprising a testing chamber with an opening at one end and two or more chambers comprising reagents at an opposite end, (b) partitions separating the testing chamber and/or the two or more chambers comprising reagents, (c) a button that interfaces with the partitions wherein pressing the button ruptures the membranes, (d) an integrated test strip, and (e) a cap assembly for inserting a specimen into the open end of the testing chamber. The device may further comprise a seal on the side of at least one of the chambers comprising reagents. The seal may be a unidirectional seal. The device will typically be self-contained. The button may comprise one or more projections which interface with the partitions.

Yet another aspect of the disclosure provides a method for detecting a disease. The method comprises the steps of (a) obtaining a specimen using a specimen collecting device, (b) inserting the specimen collection device into a self-contained diagnostic device comprising an integrated assay, (c) observing the result from the integrated assay wherein the result indicates the presence or absence of the disease with high sensitivity and specificity, and reduced testing error. For example, the method may indicate the presence or absence of the disease with a sensitivity of 92% or higher and a specificity of 95% or higher.

The self-contained diagnostic device may comprise: (a) an elongated tube comprising an opening at one end, (b) a series of chambers separated by rupturable membranes wherein the chambers comprise a testing chamber and two or more reagent chambers comprising reagents, (c) a button that interfaces with the rupturable membranes wherein pressing the button ruptures the membranes, (d) an integrated test strip, and (e) a cap assembly for inserting the specimen into the testing chamber.

The method may further comprise the steps of (a) inserting the specimen collection device into the cap assembly, (b) inserting the cap assembly comprising the specimen collection device into the self-contained diagnostic device, (c) depressing the button interfacing with the rupturable membranes on the self-contained diagnostic device wherein the membranes rupture creating a single reagent chamber open to the testing chamber wherein the reagents mix, (d) depressing the cap assembly such that the specimen collection device is inserted into the reagent chamber after the reagents have mixed, (e) inserting the integrated test strip comprising an assay through a unidirectional seal into the mixed reagent chamber, and (f) observing the test strip for the results of the assay.

The disease detected may be an infectious disease such as strep throat, influenza, whooping cough, a sexually transmitted disease such as Chlamydia or Gonorrhea, and the like.

Yet another aspect of the disclosure provides a method for detecting a disease with reduced specimen contamination and tester error. The method comprises (a) obtaining a specimen using a specimen collection device, (b) inserting the specimen collection device into a cap assembly, (c) inserting the cap assembly comprising the specimen collection device into an elongated tube comprising a testing chamber with an opening at one end and two or more reagent chambers at an opposite end wherein the testing chamber and/or two or more reagent chambers are separated by rupturable membranes, (d) pressing a button interfacing with the rupturable membranes wherein the membranes rupture, (e) inserting the specimen collection device into the reagent chamber after the reagents have mixed, (f) inserting an integrated test strip comprising an assay into the reagent chamber, (g) observing the test strip for the results of the assay, and (h) completing steps (a)-(g) in a sequential progression so as to reduce specimen contamination and tester error.

Yet another aspect of the disclosure provides a kit for detecting a disease. The kit comprises (a) a sample collection device, (b) a device comprising an elongated tube comprising an opening at one end, a series of chambers separated by rupturable membranes wherein the chambers comprise a testing chamber and two or more reagent chambers, a button that interfaces with the rupturable membranes, and an integrated test strip, and (c) written instructions for use.

Yet another aspect of the disclosure provides a self-contained device. The self-contained device comprises (a) an elongated tube comprising a testing chamber with an opening at one end and two or more chambers comprising reagents at an opposite end, (b) partitions separating the testing chamber and/or the two or more chambers comprising reagents, (c) an agent that interfaces with the partitions wherein manipulating the agent ruptures the partitions, (d) an integrated test strip, and (e) a cap assembly for inserting a specimen into the open end of the testing chamber.

Yet another aspect of the disclosure provides a testing device. The testing device comprises (a) an elongated hollow housing comprising a testing chamber with a first and second end, wherein the testing chamber comprises an opening at the first end and two or more chambers comprising reagents at the second end, (b) partitions separating the testing chamber and/or the two or more chambers comprising reagents, (c) a transfer bar adjacent to the partitions wherein manipulating the transfer bar ruptures the partitions, (d) an integrated test strip, and (e) a cap assembly removably mounted on the first end of the testing chamber for inserting a specimen into the testing chamber.

Yet another aspect of the disclosure provides a method for detecting a pathogen. The method comprises (a) inserting a sampling element with an obtained specimen into a cap assembly, (b) inserting the cap assembly comprising the sampling element with the obtained specimen into a first end of an elongated hollow housing comprising a testing chamber, wherein the testing chamber comprises an opening at the first end and two or more chambers comprising reagents at a second end wherein the testing chamber and/or the two or more reagent chambers are separated by partitions, (c) manipulating a transfer bar adjacent to the partitions wherein the partitions rupture wherein the reagents in the two or more chambers comprising the reagents mix, (d) inserting the sampling element with the obtained specimen into the mixed reagents, (e) inserting an integrated test strip into the mixed reagents, and (f) observing the test strip for test results.

Yet another aspect of the disclosure provides a method of detecting a pathogen in a non-hospital or non-clinic environment. The method comprises (a) obtaining a specimen and (b) inserting the specimen into a self-contained diagnostic device comprising a diagnostic test that produces an observable result. The diagnostic test has a specificity and/or sensitivity of at least 95% and a low error rate.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The features and advantages of example embodiments will become more apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION OF THE INVENTION

Figure 1:
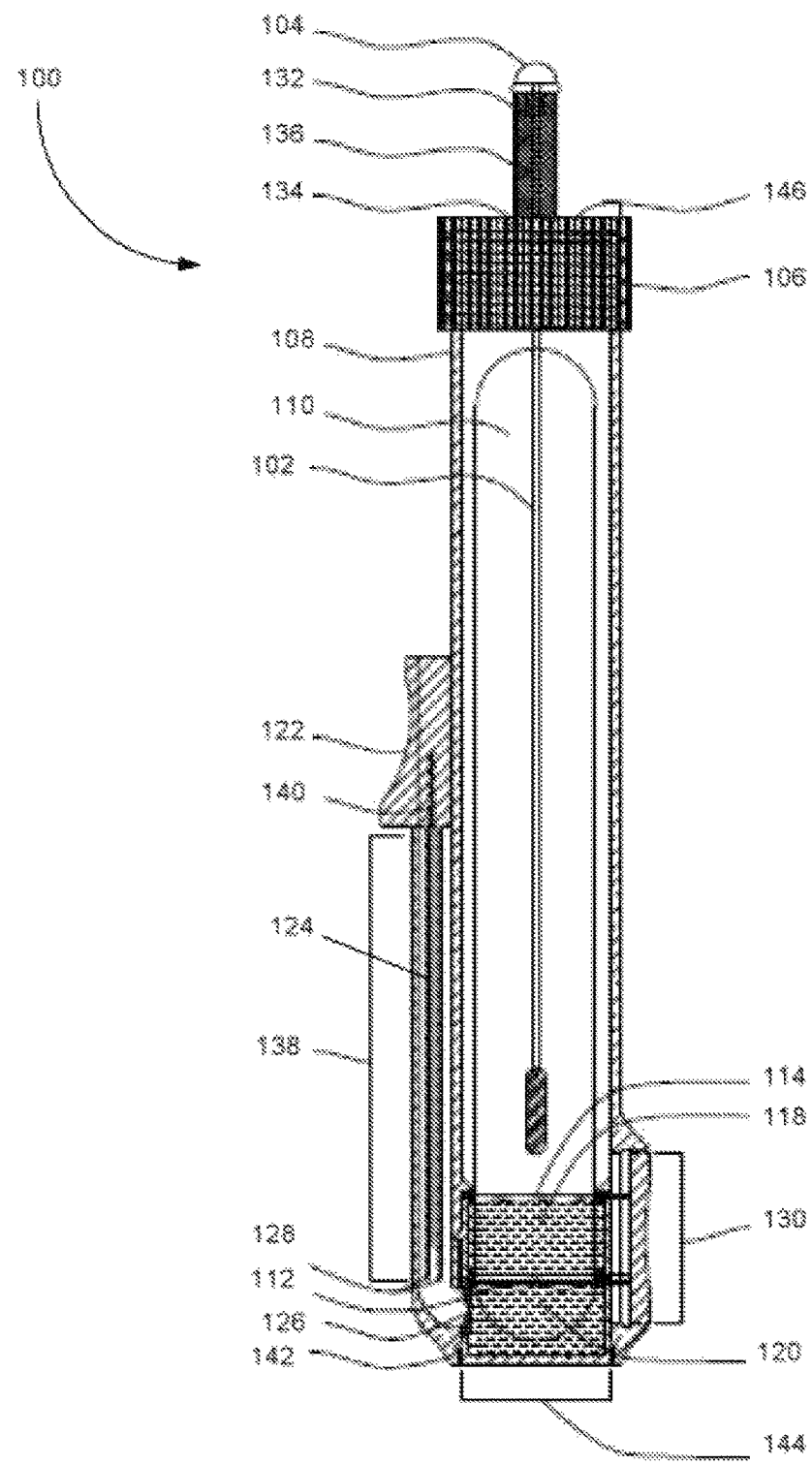
FIGS. 1 and 2 are section views of an embodiment of a self-contained screening test.

Detailed example embodiments are disclosed herein. However, specific structural and functional details disclosed herein are merely representative for purposes of describing example embodiments. Example embodiments may be embodied in many alternate forms and should not be construed as limited to only the embodiments set forth herein. Example embodiments are capable of various modifications, equivalents, and alternatives. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it may be directly connected or coupled to the other element or intervening elements may be present. By contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

In 2008, a total of 12,506,000 ambulatory care visits were made, and over 17,221,000 office visits were made for symptoms of the throat. According to the National Health Statistics Report by the Department of Health & Human Services and the Center of Disease Control, acute pharyngitis is one of the leading primary diagnoses made. Acute pharyngitis is currently the sixth most common reason patients seek physician care Further, Group A *Streptococcus* (GAS) is currently one of the most common causes of throat infections, and GAS is currently the most common respiratory infection in children. Therefore, if symptoms of throat infections are present within a patient, physicians routinely and/or commonly perform a strep test on the patient.

A self-contained screening test in accordance with many embodiments described herein comprises a qualitative, lateral flow immunoassay configured for convenient use to detect the presence of bacteria, such as streptococcal group A in a throat swab. The structure of the test unit may include a detachable tongue depressor, throat swab, specimen chamber, independent/loadable reagent capsules, and a visible test strip. Antibodies specific to a type of bacteria, such as a strep A carbohydrate antigen, may be coated on a test line region of the test strip. Upon performing a throat swab of an individual, a specimen located on the throat swab may migrate or be disposed on the test strip. If the antigen is present in the sample, the antigen may react with the bacteria antibody on the test strip to form a complex. The reaction may produce a visible color change on the test strip to indicate a positive result or detection of the bacteria, such as streptococcal group A. For example, if a sample specimen from a throat swab migrates along a test strip, and a Group A strep antigen is present in the specimen, a reaction will form a complex with the antigen A strep antibody on the test strip. The complex will then bind to the test strip and form a visible line to indicate a positive reading on the test strip.

The testing unit may have a sensitivity of over ninety-five percent, which is high enough to be used reliably in a point of care setting without having to take extra, unnecessary or additional back-up cultures. The testing unit may have a shelf life of approximately fourteen months from the date of manufacture at room temperature. In some embodiments, based on the components and antigens, different testing units may have different expiration periods.

The testing unit allows for a quick detection of bacteria such as streptococcal, which is a common cause of sore throats, thus allowing for more immediate treatment. A positive culture may require antibiotic treatments to reduce symptoms, shorten duration of illness and eliminate a possibility of spread of infection. Individuals may reliably screen for the presence of bacteria in convenient locations and avoid extra costs associated with a visit to a doctor and/or hospital.

Oral fluid samples may contain antibodies or antigens to various diseases, including bacterial infections and sexually transmitted diseases, for example *streptococcus* group A, influenza A and B, human immunodeficiency virus (HIV), Hepatitis B, Rubella, cytomegalovirus (CMV), hepatitis C virus (HCV), toxoplasmosis, hepatitis A virus (HAV), Lyme disease, Candida, Bacterial Vaginosis, HPV, testing for drug abuse, therapeutic drug monitoring, or DNA diagnostics.

The test sample may be derived from any biological source, such as physiological fluid, including blood, interstitial fluid, saliva, sweat, urine, milk, ascites fluid, mucous, synovial fluid, peritoneal fluid, vaginal fluid, amniotic fluid, and the like.

Besides physiological fluids, other liquid samples may be used such as water, food products, and the like for the performance of environmental or food production assays. Such swabbing may be done in a food service area to determine the presence or absence of environmental or food pathogens or contaminants.

The term "analyte" used herein may generally refer to a substance to be detected. For instance, analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances. Specific examples of some analytes include ferritin, creatinine kinase MB (CK-MB), digoxin, phenytoin, phenobarbitol, carbamazepine, vancomycin, gentamycin, theophylline, valproic acid, quinidine, lueteinizing hormone (LH), follicle stimulating hormone (FSH), estradiol, progesterone, C-reactive protein, lipocalins, IgE antibodies, cytokines, vitamin B2 micro-globulin, glycated hemoglobin (Gly. Hb), cortisol, digitoxin, N-acetylprocainamide (NAPA), procainamide, antibodies to rubella (such as rubella-IgG and rubella IgM), antibodies to toxoplasmosis (such as toxoplasmosis IgG (Toxo-IgG) and toxoplasmosis IgM (Toxo-IgM), testosterone, salicylates, acetaminophen, hepatitis B virus surface antigen (HBsAg), antibodies to hepatitis B core antigen, such as anti-hepatitis B core antigen IgG and IgM (Anti-HBC), human immunodeficiency virus 1 and 2 (HIV 1 and 2), human T-cell leukemia virus 1 and 2 (HTLV), hepatitis B e antigen (HBeAg), antibodies to hepatitis B e antigen (Anti-HBe), influenza virus, thyroid stimulating hormone (TSH), thyroxine (T4), total triiodothyronine (Total T3), free triiodothyronine (Free T3), carcinogembryoic antigen (CEA), lipoproteins, cholesterol, triglycerides, and alpha fetoprotein (AFP).

Examples of various reagents which may be used to detect and identify microorganisms include one or more of various well known test reagents. Such reagents may be present in either liquid or solid/powder form. The particular test reagent used may be chosen on the basis of the particular type of microorganism species being identified or tissue cells being tested. Commercially available reagents may be used. For example, a test reagent such as N,N,N,N tetra methyl-p-phenylenediamine dihydrochloride may be used for detecting gonorrhea. Other test reagents such as dimethyl amino-cinnaminaldehyde, beta b galactosidase substrates, gamma glutamylamino peptidase and prolylamine peptidase may also be used for detecting specific species of the genus *Neisseria*. Further test reagents may include, but are not limited to, hippuric acid for detecting Group B *Streptococcus*, L-pyrrolidonyl beta naphthylamide and esculin for detecting Group A *Streptococcus*, and acid or mineral acids, such as citric, acetic, and hydropchloric acid and sodium nitrite, for detecting Group A *Streptococcus* antigen.

Tests according to many embodiments described herein apply immunoassay technology, which involves the interaction of a fixed reagent of either target antigen or antibody that is linked to some type of visible detector that then reacts with a patient sample. Such immunoassay technology can be used for many indications.

In many embodiments, strep A is tested for. The self-contained test may comprise a qualitative, lateral flow immunoassay utilized for the detection of Strep A carbohydrate antigen in a throat swab. An antibody specific to Strep A carbohydrate antigen may be coated on test line region of visible test strip. A sample specimen from the throat swab may migrate along the test strip. If Group A Strep antigen is present in the sample, it may form a complex with the anti-group A strep antibody on the test strip. The complex may then bind and form a visible red test line to indicate positive reading. Reagent A, for example, may comprise 2M sodium nitrate. Reagent B, for example, may comprise 0.3M acetic acid.

In many embodiments, influenza is tested for. A preferred sample may comprise a nasal aspirate, but the most frequently used sample may comprise the nasopharyngeal (NP) swab. Influenza type A and B antigen may be detected by a direct fluorescent antibody (DFA). Influenza type A and B antibodies (IgM, IgG) may be coated on the test line region of a test strip. The Influenza A reagent may comprise a FITC labeled influenza A antibody, protein stabilizer, Evans blue, and 0.1% sodium azide (preservative). The Influenza B reagent may comprise a FITC labeled influenza B antibody, protein stabilizer, Evans blue, and 0.1% sodium azide.

In many embodiments, Gonorrhea is tested for and the reagent used may comprise N,N,N,N tetra methyl-p-phenylenediamine dihydrochloride.

In many embodiments, *Neisseria* is tested for and the reagent used may comprise Dimethyl amino-cinnaminaldehyde, Beta d galactosidase substrates, Gamme glutamylamino peptidase, and Prolylamine peptidase.

In many embodiments, Group A *Streptococcus* is tested for and the reagent used may comprise Huppuric acid.

In many embodiments, Hepatitis B is tested for, the target antigen may comprise HBsAg, the analyte type may comprise an antigen detection test, and the reagent used may comprise Anti-HAV IgG, Anti-HAV IgM, Anti-HBc, Anti-HBc IgM, Anti-HBs, Anti-HCV, or HBsAg.

In many embodiments, HIV is tested for, the target antigen may comprise HIV 1/2 antigen, the analyte type may comprise antibodies (serology test), and the reagent used may comprise Anti-HIV-1/HIV-2, Anti-HTLV-1/HTLV-II, or HIV Ag/Ab Combo.

In many embodiments, malaria is tested for and the target antigen may comprise HRP2 or PLDH.

In many embodiments, syphilis is tested for, the target antigen may have a size of 15, 17, or 47 kDa, and the analyte type may comprise antibodies.

In alternative embodiments, many other diseases or physical conditions may be tested for and biomarkers used, including: Allergy, Anemia, Cardiac Markers, Chagas Disease, Chlamydia, Cholera, Dengue, DIC Markers, *E. coli*, Fertility, Filiariasis, Group A *Streptococcus*, Group B *Streptococcus*, Hantavirus, Hepatitis C, Influenza A, Leishmaniasis, Leptospirosis, Listeria, Peptic ulcer, Rheumatoid Factor, Rickettsia, Salmonella, Thyroid Markers, Tuberculosis, and Tumor Markers.

Turning now to FIG. 1, depicted is an embodiment of a self-contained test 100. Self-contained test 100 may be configured to analyze a throat specimen for the detection of bacteria, such as streptococcal group A bacteria. Self-contained test 100 may be a qualitative, lateral flow immunoassay utilized for the detection of bacteria on a throat swab 102.

Test 100 may include an easy grip throat swab 102, a collapsible pop top 104, a dispenser cap 106, test tube 108, a removable tongue depressor 110, a preloaded reagent capsule for reagent A 118 with top breakaway divider 114 and bottom breakaway divider 115, a reagent capsule for reagent B 120 with breakaway divider 116, lever 122, test strip 124, uni-directional seal entry 126, test strip cover 128, and button 130. The throat swab 102 may comprise a sterile rayon-tipped swab disposed on a solid plastic shaft, which may fit one or more ergonomic criteria such as by comprising a rubber grip. The breakaway dividers may be made of rigid but brittle materials, such that squeezing the breakaway dividers (compressing them from the side) results in fracturing and collapse of the breakaway dividers. In other embodiments, the capsules 118, 120 comprise vacuformed blister packs also known as crush packs, that once broken, lie flat, similar to bubble wrap.

Tube 108 may be an open test tube with a loadable base. The test tube 108 may have an open base 144 with an internal track system to allow different reagent capsules to be loaded into test tube 108. Accordingly, different diagnostic tests may be performed using test 100 based on the capsules that are loaded into tube 108 (e.g. strep, influenza, pertussis, or various vaginal infections/STDs). Test procedures are generally the same for different bacteria, although the number of capsules and type of swab and reagents may vary. The location on the tester's body where the sample is collected may also vary, as well as the amount of time the reagents must mix with the sample and the amount of time the test strip must be exposed to this mixture.

Dispenser cap 106 may be comprised of plastic (or any other suitable material, such as metal or rubber), have a rubber (or other suitable material) ridged easy-grip handle 136 and be configured for holding swab 102, such as with a frictional or interference fit. By using a ridged handle, a tester or test administrator may more easily obtain a throat culture using swab 102, compared with holding the edge of a wide round cap or smooth slippery surface. Furthermore, the body of dispenser cap 106 may be designed to include collapsible pop top 104 coupled to swab 102 via attachment sleeve 132. A pop top is a projection that can move between a first, extended position and a second, collapsed position in which the body of the pop top is inserted within the object it projects from, with only the top of the pop top showing above the surface of the object. Pop top 104 can be collapsed, which may extend swab 102 forward into a mixture. The collapsible pop top 104 may include indented channel locks 134 with raised ridges to keep the pop top collapsed 104 once in a collapsed position. The ridge 133 on pop-top 104 snaps into channel lock/clip 134 when the pop-top is depressed, preventing the pop-top from being moved out of the depressed condition. If collapsible pop top 104 is in a collapsed position, dispenser cap 106 may lock, providing a testing chamber control device and/or safety mechanism that may prevent, limit or stop testing components from leaving tube 108. Cap 106 may also include a threaded lock. The locking mechanism ensures that testers are not exposed to chemicals at any point during testing, and that samples are always sealed. This increases the safety and the accuracy of test results.

Pushing and/or pressing down on pop top 104 may cause movement of swab 102 within test tube 108 to ensure timely exposure of a biological sample disposed on a bottom portion of swab 102 to reagents 118, 120 for a possible reaction to take place.

Test tube 108 may be a tubular housing device with an open face. In different embodiments, tube 108 may vary in size, shape and/or design. The tube 108 may comprise solid color, opaque polypropylene, ABS plastic, or a regulatory agency or otherwise approved equivalent. Tube 108 may be comprised of a long chamber having an opening at a base 144, with an inner track system that allows for reagent capsules 118, 120 to be individually loaded via base 144 of tube 108. Upon capsules 118 and 120 being loaded within tube 108, a top surface of capsule 120 may be adjacent to a bottom surface of capsule 118. Furthermore, the reagent capsules 118, 120 may be placed at a bottom portion of tube 108, such that if push top 104 is not in a collapsed position, swab 102 does not touch or is not within reagent capsules 118 or 120.

Each of the reagent capsules 118, 120 may be configured to be pre-loaded with reagent(s), such that reagent(s) are stored in different chambers or capsules. Therefore, capsules 118, 120 may be pre-loaded with reagents one at a time through the track within the opening at the base 144 of tube 108, and as many capsules as are needed, required or desired may be individually loaded within tube 108. By filling each capsule with different reagents, test 100 may be configured to detect the presence of different bacteria. Accordingly, a test kit may be manufactured and/or packaged to include a test that may be configured to detect different kinds of bacteria based on the reagent capsules loaded into tube 108.

The separation of the reagents within different capsules or chambers allows for proper mixing of reagents at appropriate times. This increases the reliability and/or accuracy of the test. Also, the chemical reagents are not exposed to an open portion of tube 108, while being disposed within a capsule that is unbroken. For example, if the test tube 108 is turned upside down or set horizontally on its side with the cap off, such as while a culture is being collected, no chemical will spill or contaminate the test chamber, or mix with other reagents. Further, the reagents will only be exposed once dispenser cap 106 is placed on tube 108, sealed in a locked position, and button 130 is pressed thereby breaking dividers 114, 115, 116 between the reagent capsules and between the capsules and the interior of the test chamber. Accordingly, having each capsule sealed with a reagent provides a major manufacturing/packaging advantage because the product may be shaken and/or turned upside while being transported to an end user without compromising the test 100.

Furthermore, reagent capsule 120 disposed at the base of tube 108 may include a one-way pierced rubber seal entry. Rubber seal entry 126 may be disposed along a vertical side of reagent capsule 120 and may be aligned with an opening of a sidewall of tube 108. Rubber seal entry 126 may be configured as a uni-directional flow entry, allowing test strip 124 and plastic coverings 128 to open or pierce rubber seal entry 126 without reagents or any other chemicals leaving reagent capsules 118, 120, and/or tube 108 (except between the plastic coverings 128). Accordingly, rubber seal entry 126 may be configured to allow test strip 124 and/or plastic covers 128 to pierce seal entry 126 to enter the sample mixture/reagents. More specifically, rubber seal entry 126 may have rubber projections that bend open when pierced by an object, but seal against the inserted object and may be re-sealed and/or bend to be in a closed position upon the piercing object being retracted. In some embodiments, seal entry 126 may be made of a material other than rubber, for example another flexible but firm material such as silicone.

Test tube 108 may also include button 130. Button 130 may be a compression button disposed at a sidewall of a lower portion of tube 108. Button 130 may be positioned such that projections of button 130 are aligned with the top surface of capsule 120 and the top and bottom surface of capsule 118 when the capsules 118 and 120 are loaded within tube 108. Furthermore, button 130 may be shaped with an outlined fingerprint indentation or depression 131. The outlined fingerprint indentation or depression may indicate to the user to "push here" or "press here." Upon a user pressing the outlined indentation, the dividers between the reagent capsules 118 and 120 may break, and a divider between the test tube 108 and the top reagent capsule 118 may break as well.

The capsules 118, 120 may be broken within test tube 108 without swab 102 having to pierce through a seal, divider, or saran wrap. This may ensure that none of the sample throat culture will be lost and/or wiped away because the swab 102 is not used to break any divider or pass through a seal. Accordingly, an adequate amount of biological sample will be retained for testing and mixing with the reagents.

In alternative embodiments, the swab itself may be used to break dividers or seals between the compartments and/or between one or more compartments and the main body of the test tube 108. For example, a plastic flap or rubber seal may separate the interior of the test chamber from the capsules 118, 120, and the swab 102 may be used to break this barrier and insert the test specimen into the reagents.

The button as illustrated can be designed so that it is difficult to press the button inadvertently, therefore releasing the chemicals before a tester is ready, for example while the top of the testing chamber is open. Projections from the testing chamber above and below the button can ensure that the button is essentially flush with the testing chamber around it, and therefore little force is exerted on the button when pressed against a surface that extends beyond the length of the button. Furthermore, a considerable amount of force may be required to move the button from a first position to a second, pressed position. Projections from the sides of the button move from one set of notches to another with a snap when the button changes positions. Therefore, it is unlikely that the button would be pressed, moving from a first to a second position and opening the breakaway dividers, without deliberate application of force directly to the button. Furthermore, the button may move from a first position to a second with an audible click, alerting the tester that the capsules have been opened (other movements, such as depressing and locking the pop top, may also emit an audible click or other noise to confirm locking). Mixing of the chemicals in the capsules may also result in a color change, providing a visible alert.

In other embodiments, other means are used to prevent inadvertent pressing of the button, such as a removable locking tab or other removable/releasable locking device. A soft, easily pressable button may be used in some embodiments, with or without such safeguards.

Test 100 may also include a test strip compartment 138 configured to house movable test strip 124 mounted on a sliding track. Test strip compartment 138 is not housed or positioned within test tube 108, which adds an additional level of protection to test 100 by decreasing the risk of prematurely exposing test strip 124 to a biological sample, chemical reagents, or contamination by way of manual handling. Test strip compartment 138 may be a plastic cover on a side of tube 108. On an upper surface of test strip compartment 138 may be disposed a simple lever 122 shaped to receive pressure from a finger. Lever 122 may be coupled to a top portion of testing strip 124. To aid the transportation of test strip 124, test strip 124 may be coupled to lever 122 via an alligator grip lock 140 which holds test strip 124 in place. The alligator grip lock 140 may secure the test strip 124 such that the test strip 124 may slide up and down a track to enter seal 126, be exposed to a sample, and return to its original position. As such, test strip compartment 138 may be configured as a guide to bend and/or direct test strip 124, so that test strip 124 enters rubber seal entry 126.

Plastic coverings 128 may surround or border the test strip 124. These coverings may be just on two sides of the test strip, or may encircle the test strip or also be on two other sides of the test strip, and may be integrally formed with the sliding tab or may also be secured with the alligator clip. They may be directly adjacent to the test strip, or the seal entry may force the coverings against the test strip where they penetrate the seal entry, and/or the coverings may extend the width of the test strip compartment, preventing leakage of chemicals from the capsules into the test strip compartment. A lower portion of plastic coverings 128 may extend past a lower portion of the test strip 124. Accordingly, if force is applied to lever 122, test strip 124 and plastic coverings 128 may slide along a track and pierce, puncture or penetrate rubber seal entry 126. The plastic coverings 128 protect the integrity of the test strip 124 during penetration of the rubber seal entry 126. The lower portion of plastic coverings 128 may be left open, which allows for an upward flow of the sample fluids along the body of test strip 124 after the plastic coverings 128 have pierced rubber seal entry 126. Test strip 124 and coverings 128 may be configured such that if coverings 128 have penetrated rubber seal entry 126, then sample fluids and reagents will be contained within the plastic coverings 128, and at no point will fluids, chemicals and/or reagents spill or be exposed to an individual performing the test, the environment outside of tube 108, or a tester. Thus, the reliability of the test results may be increased while ensuring greater safety and improved disposal of test 100 components.

Test strip 124 and coverings 128 may retract back into their original position outside of tube 108, within housing 138, after coverings 128 have pierced rubber seal entry 126, and test strip 124 has been exposed to the fluid within tube 108. This may allow a tester a more clear view of test strip 124 to ensure a more reliable and easier reading of test strip 124 (housing 138 may be transparent).

In alternative embodiments, other methods may be used to insert the test strip into the reagent mixture besides the track, sliding tab, and test strip compartment. For example, the test strip may be inserted through the top or through a hinged or otherwise movable opening in a side of the testing chamber.

Test 100 may also include a detachable tongue depressor 110. Detachable tongue depressor 110 may be a plastic tongue depressor with rounded edges that is mounted or removable coupled to a back side of tube 108, for example using an adhesive or mounting clips. Tongue depressor 110 may be configured to peel back and off tube 108, thus separating tongue depressor 110 from tube 108. Tongue depressor 110 may be configured to be used during the collection of a throat culture. By depressing the tongue of a person being tested, the sample taker may have greater access to the back of the throat. As a result, it is easier for the tester to obtain a better sample.

In further example embodiments, cap 106 may include a pre-set timer 146. In one embodiment, by twisting cap 106 ninety degrees after test strip 124 has been immersed in fluids, a preset timer may begin. More specifically, timer 146 may be a timer unit with a built-in alarm to alert a tester that results may be accurately and reliably read. For example, if cap 106 is twisted ninety degrees the preset time 146 may begin, and a tone may sound to indicate a wait time has passed and the test strip is ready to display the results.

Figure 2:
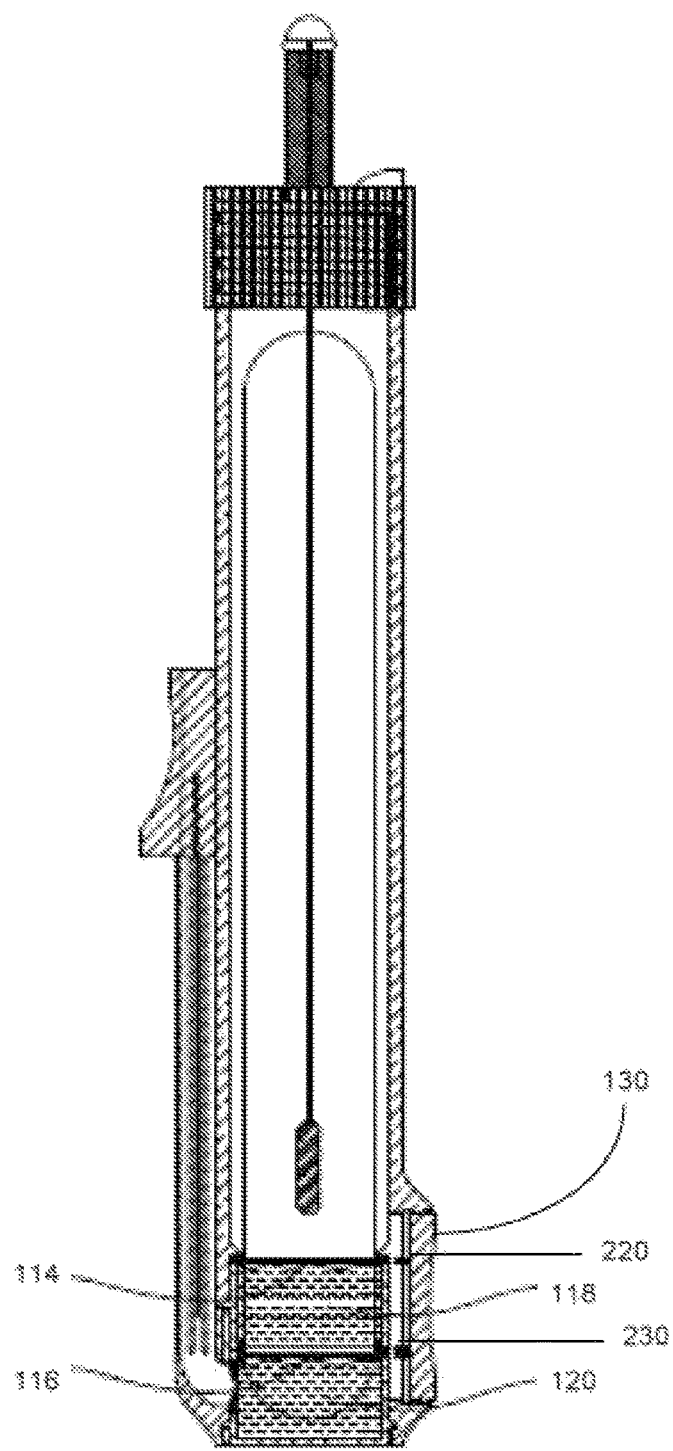

FIG. 2 depicts another embodiment of test 100. As depicted in FIG. 2, reagent capsule 118 has breakaway dividers 114, 115 disposed at a top and bottom surfaces of capsule 118. Breakaway divider 114 may separate reagents in capsule 118 from the rest of the test tube chamber 108. Breakaway divider 115 (in addition to breakaway divider 116) may separate reagents in capsule 118 from reagents in capsule 120. Similarly, reagent capsule 120 may have a breakaway divider 116 disposed at a top surface of capsule 120.

The bottom 210 of capsule 120 is not a breakaway divider, because capsule 120 is intended to be the bottom-most of the capsules and accidental leakage of reagent out the bottom of capsule 120 is to be avoided. In other embodiments, to save manufacturing cost or for flexibility, the capsules may have similar or identical structure, with for example breakaway dividers on the top and bottom. In such an embodiment, the test chamber might have a bottom hinged door (or other closure) that can be closed after insertion of the capsules to prevent such inadvertent breakage.

Figure 3:
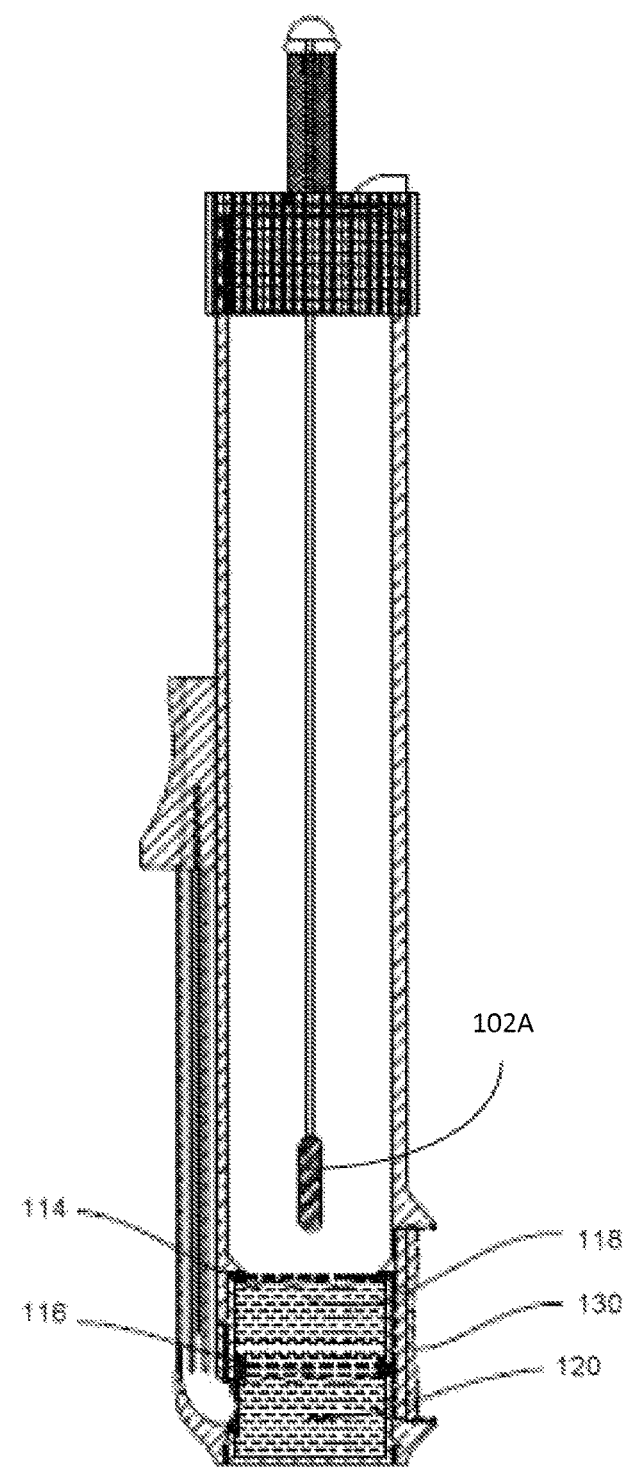
FIG. 3 is a section view of an embodiment of a self-contained screening test after pressure has been applied to a button.

The breakaway dividers 114, 115, 116 allow for reagent capsules 118, 120 to be broken to dispose reagents within tube 108 without contacting swab 102. Therefore, no medical sample of a tester on swab 102 will be lost or contaminated by having to break through a seal. To break or pierce breakaway dividers 114, 115, 116, button 130 may include projections 220 and 230. Upon button 130 receiving force or being pressed inward towards the center of tube 108, projections 220 and 230 may be received by breakaway dividers 114, 115, 116, respectfully, puncturing them as shown in FIG. 3. Subsequently, the chemicals/reagents within capsules 118, 120 may mix. As such, one skilled in the art will appreciate that in test 100, swab 102 is not used to puncture or touch breakaway dividers 114, 115, 116 corresponding to reagent capsules 118, 120, respectfully.

FIG. 3 depicts another example embodiment of test 100, where pressure has been applied to button 130. Upon pressure being applied to button 130, projections 220 and 230 may be inserted into capsules 118, 120 to puncture or break dividers 114, 115, 116, respectfully, as illustrated. The chemicals/reagents within capsules 118, 120 may then mix. In alternative embodiments, other devices or mechanisms may be used for breaking the capsules. For example, a portion of the capsules may be accessible from outside the test chamber, and a user may manually squeeze or otherwise manipulate the capsules in order to open them in or more places.

Figure 4:
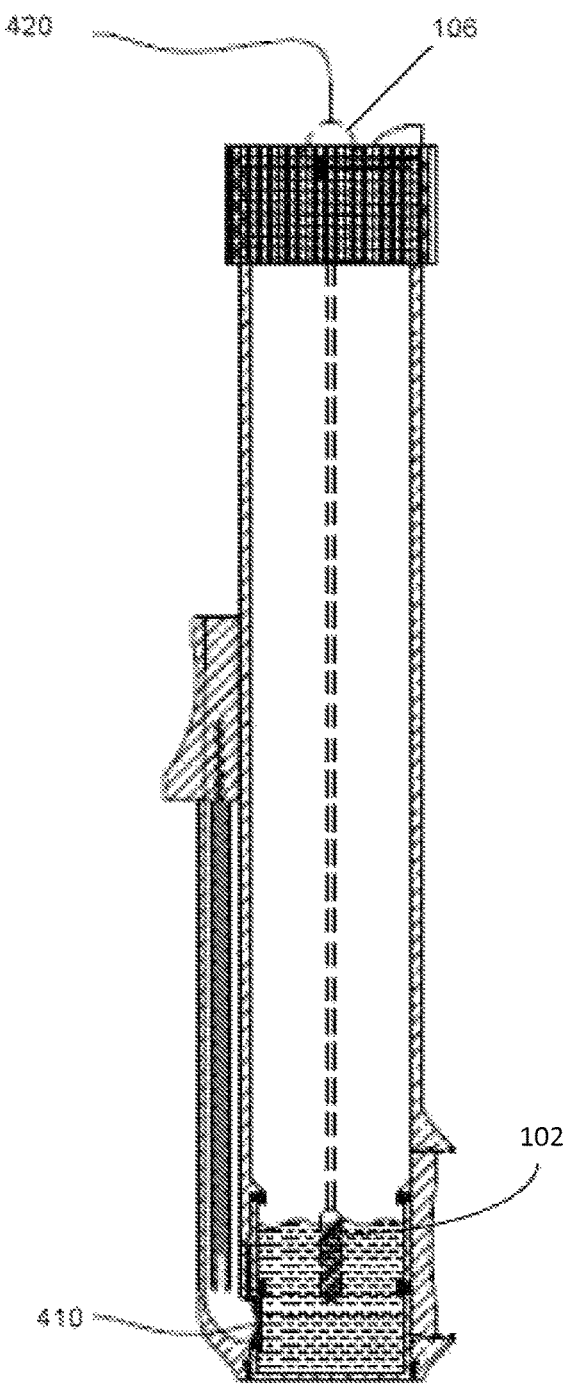
FIG. 4 is a section view of an embodiment of a self-contained screening test after breakaway capsule dividers have been ruptured and a test swab has been inserted in the capsules.

FIG. 4 depicts an example embodiment of test 100 after button 130 has been pressed inward, breaking the reagent capsules and mixing the chemicals within the capsules. Once the chemicals within the broken capsules have mixed, swab 102 with the specimen may enter the mixture 410 when a tester presses push top 104 into a collapsed position 420. When push top 104 is placed into collapsed position 420, the swab tip 102A is inserted into mixture 410 with the chemical reagents. In other embodiments, the swab tip 102A could be spring-loaded or telescoping for forward extension (and e.g. button-activated) or can be manually inserted with an open top or other orifice, despite the inherent drawbacks of such a procedure.

Figure 5:
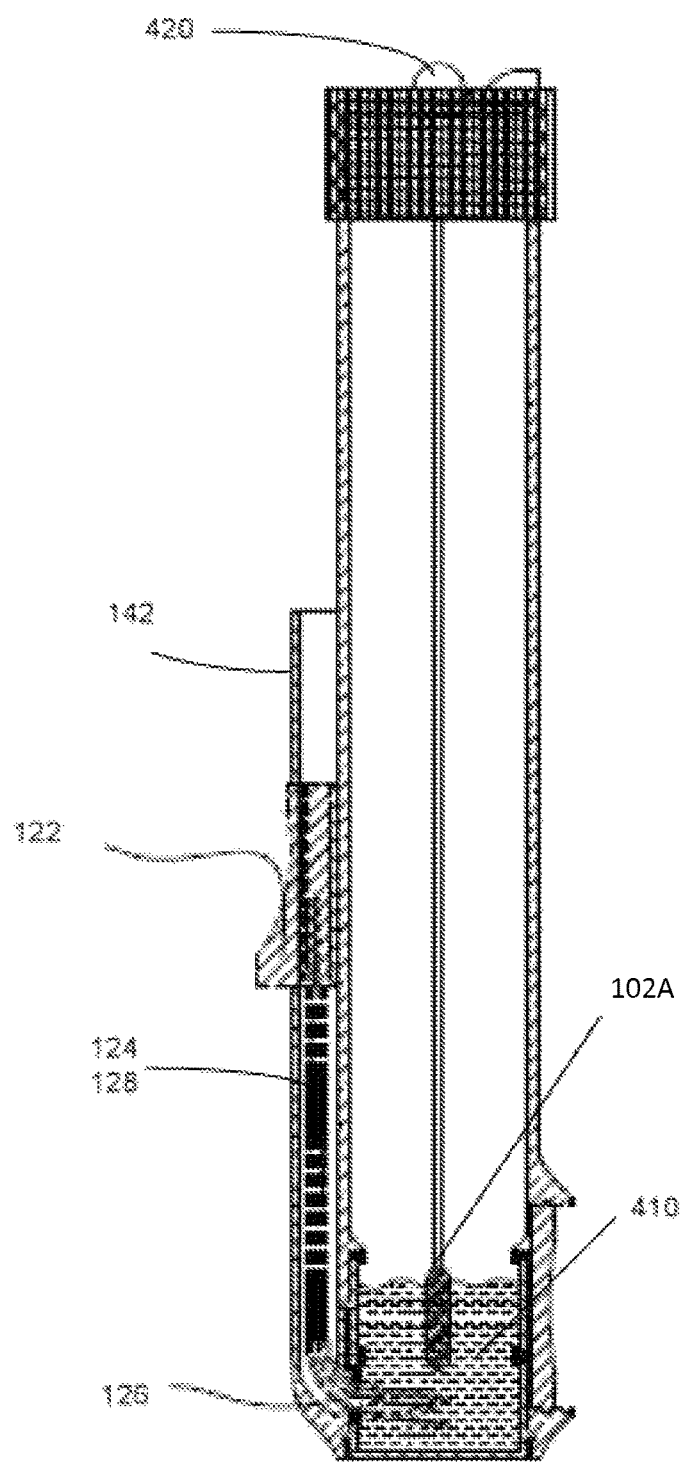
FIG. 5 is a section view of an embodiment of a self-contained screening test after a test strip has been inserted in the capsules.

FIG. 5 depicts an example embodiment of test strip 124 being inserted into mixture 410. When lever 122 is pressed, coverings 128 and test strip 124 may slide in a downward motion along track 502, pierce through rubber seal entry 126 and be disposed into mixture 410. While test strip 124 is disposed within mixture 410 with the specimen on swab 102, test strip 124 may interact with mixture 410 and a throat culture on swab 102 so that test strip 124 may yield a visual result. In other embodiments, the test strip 124 may be rigid/sturdy enough to be inserted and withdrawn without any coverings.

Figure 6:
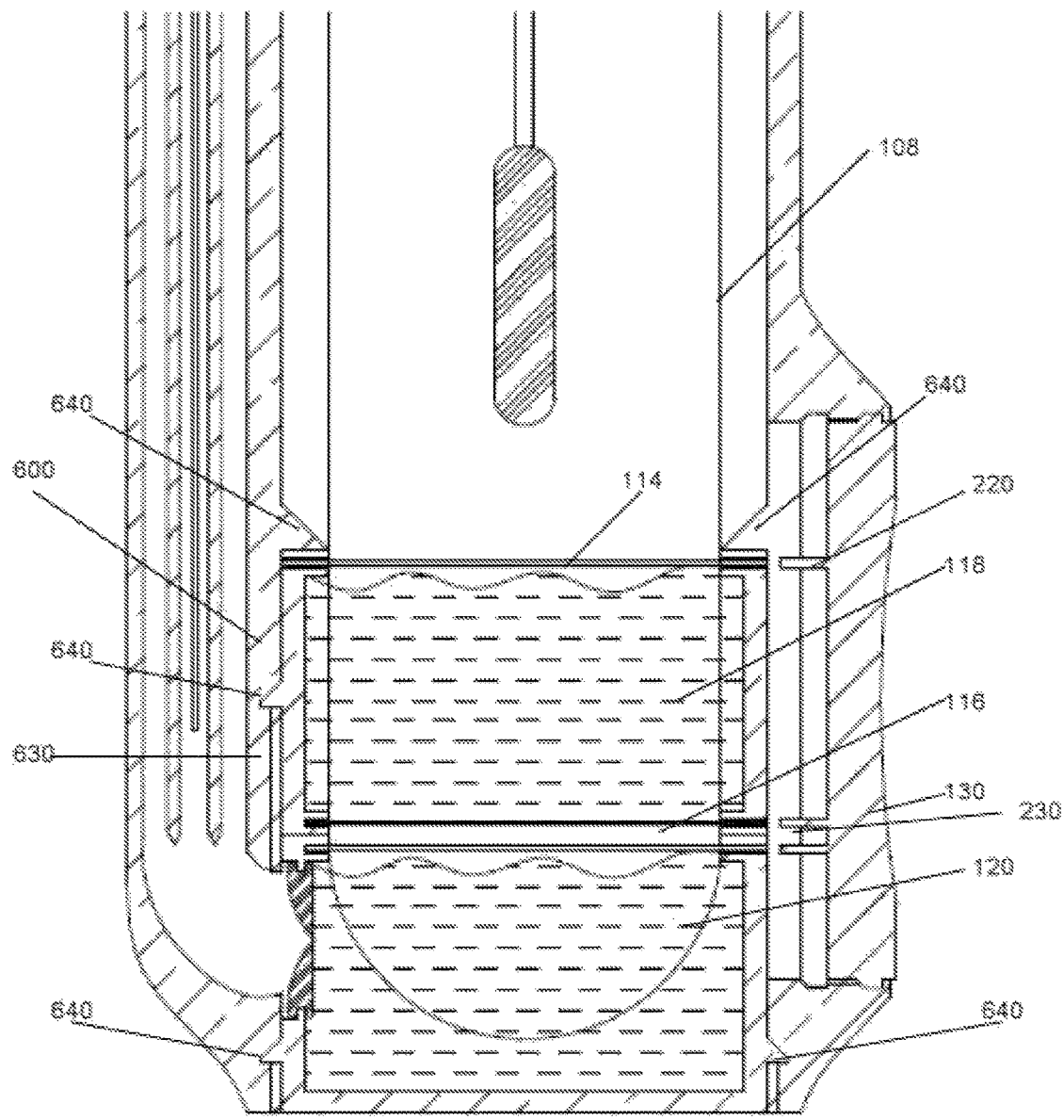
FIG. 6 is a detail section view of the base of an embodiment of a self-contained screening test.

FIG. 6 is a detail view of the base of an embodiment of tube 108 having orifice 144. Base chamber 600 may be disposed at the base of tube 108 and be aligned with orifice 144. Reagent capsule 118 has breakaway dividers 114, 115 disposed at its top and bottom surfaces, and reagent capsule 120 has breakaway divider 116 disposed at a top surface of capsule 120 and a seal entry 126 on one side. More specifically, capsule 118 may correspond to a first reagent that may be comprised of 2M of sodium nitrate, while reagent capsule 120 may correspond to a second reagent that may be comprised of 0.3M of acetic acid. As illustrated in FIG. 6, button 130 includes projections 220 and 230 corresponding to capsule 118 and 120 respectfully. Upon pressure being applied to button 130, projections 220 and 230 may pinch the breakaway dividers 114, 115, 116 to release or break the dividers. Then the reagents may combine and mix.

FIG. 6 depicts tube 108 having a sliding track 630 with stop 810 and stop locks 640. Stop locks 640 may be configured to snap and hold reagents capsules in place once they are disposed within tube 108. Accordingly, multiple and variable reagent capsules may be loaded into tube 108 based on the type of diagnostic test required or desired by a tester. In this embodiment, the stop locks for each capsule (top and bottom) are unique, so a capsule intended to be used on the bottom will not fit in the top position and vice versa. In other embodiments, all capsules may use the same stop locks. Also, in some embodiments the base chamber 600 may have space and stop locks for three or more capsules. Such an embodiment may nevertheless be used with only one or two capsules, as the seal entry may be on the first or second capsule and the bottom of the first or second capsule may be rigid and not break when the button is pressed.

Figure 7:
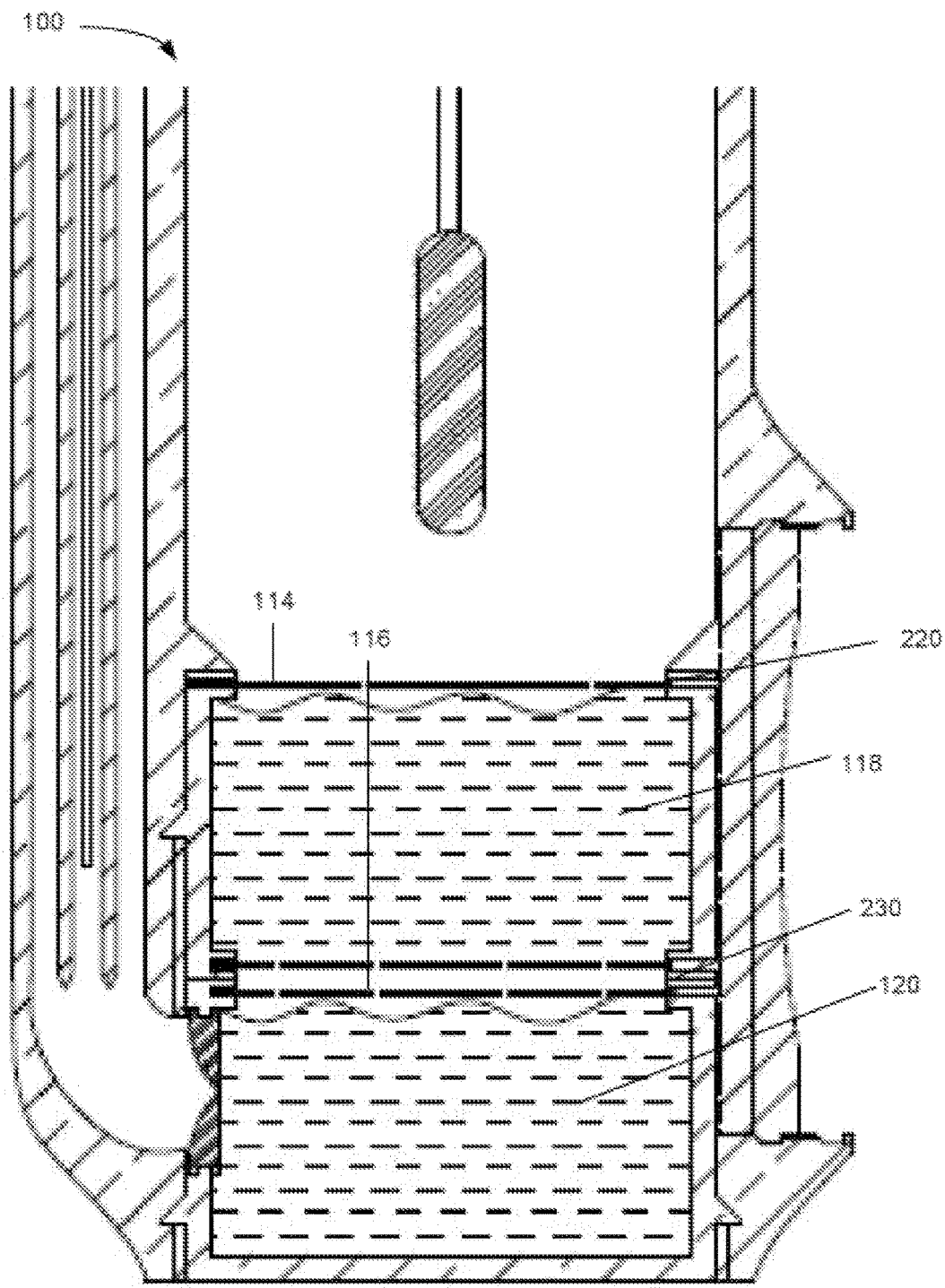
FIG. 7 is a detail section view of the base of an embodiment of a self-contained screening test after a button has been pressed.

FIG. 7 is a detail view of the base of an embodiment of tube 108 where button 130 has been pressed inward to break the reagent capsules and mix the chemicals within the capsules 118, 120. Projections 220 and 230 have been received by breakaway dividers 114, 116, respectfully, and have punctured them. The chemical(s)/reagent(s) within capsule 118 will thereafter drop into capsule 120 and mix with the reagent(s) contained there. In other embodiments, other methods for mixing the capsules may be used besides breakaway dividers and pinching projections. For example, a sharp object may be thrust through both capsules to release and mix their contents, or the capsules may have closures that open electronically with the push of a button, and may be powered by the test chamber.

Figure 8:
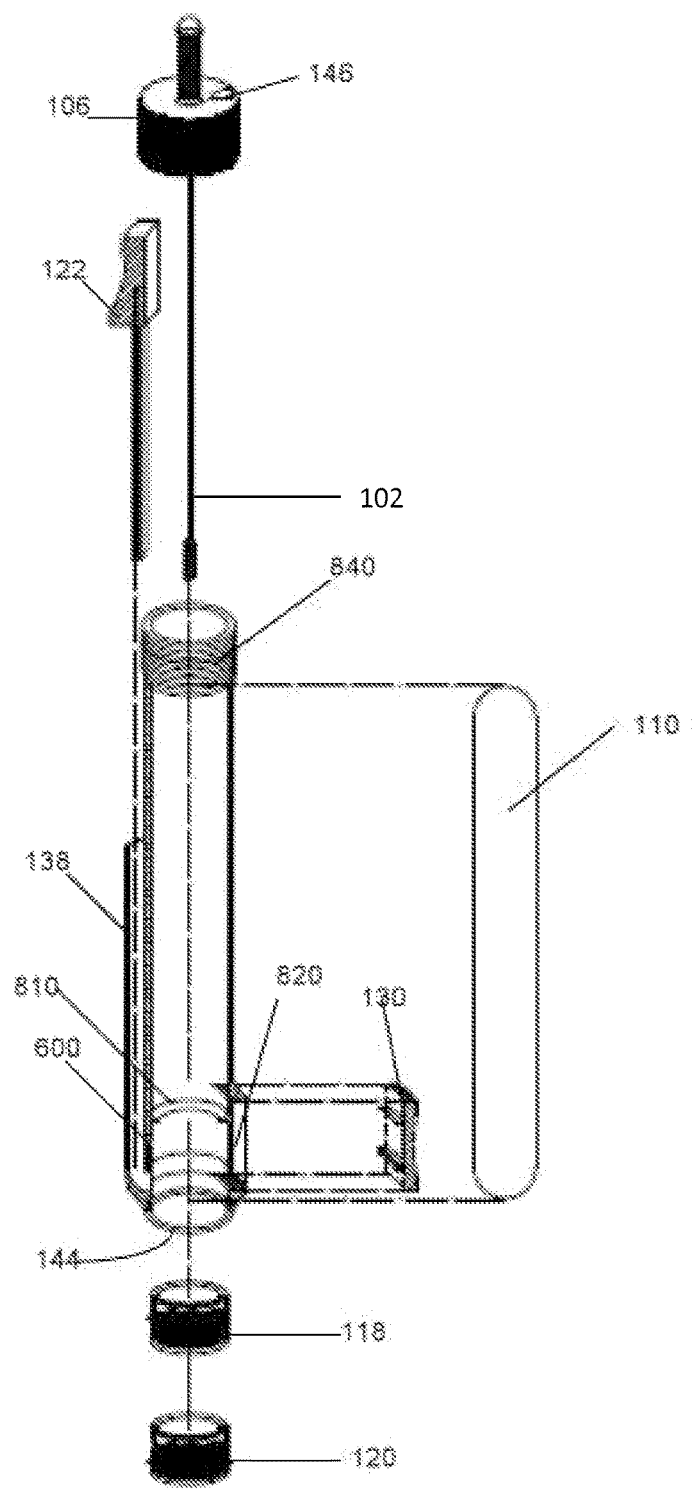
FIG. 8 is an exploded view of an embodiment of a self-contained screening test.

FIG. 8 is an exploded view of an embodiment of a test 100. FIG. 8 depicts tube 108 having an open base 144. Within opening 144 is chamber 600 configured to receive reagents capsules 118, 120. At the top of chamber 600 is stop 810 configured to prevent movement of capsules further into the test chamber and below that are stop locks 640 configured to secure and/or hold capsules 118, 120 within tube 108. Also FIG. 8 depicts slot 820 configured to receive button 130. As shown in FIG. 8, lever 122 is coupled to test strip 124 and coverings 128 and may be configured to be disposed within test strip housing 138.

Furthermore, tube 108 may include a threaded mouth 840 configured to receive cap 106. Tongue depressor 110 may be configured to be disposed to a back side of tube 108.

Embodiments of the self-diagnostic test may be one-time-use or reusable. In some embodiments, the test is one-time use only, as stop locks prevent removal of capsules once inserted and/or a channel lock and threaded lock maintain a pop-top and cap in place, respectively, after the pop-top is depressed, and/or the test strip housing is closed off and does not allow the test strip to be replaced. This may allow for the test to be completely and permanently sealed off after the testing process begins, and may also allow use of less expensive materials and encourage return purchases. However, in other embodiments the test is designed to be reusable, which may provide significant cost savings for frequent testers. In such embodiments, the test strip, swab, and capsules are removable and replaceable. In such embodiments, there may be an ejection button for removing spent capsules, the pop-top or channel lock and threaded lock may be omitted, and the test strip lever may be removable for replacing spent test strips. In such embodiments, various locking structures can be made to hold only until sufficient force is provided (unlikely to occur without deliberate effort), or until a release mechanism is triggered.

Figure 9:
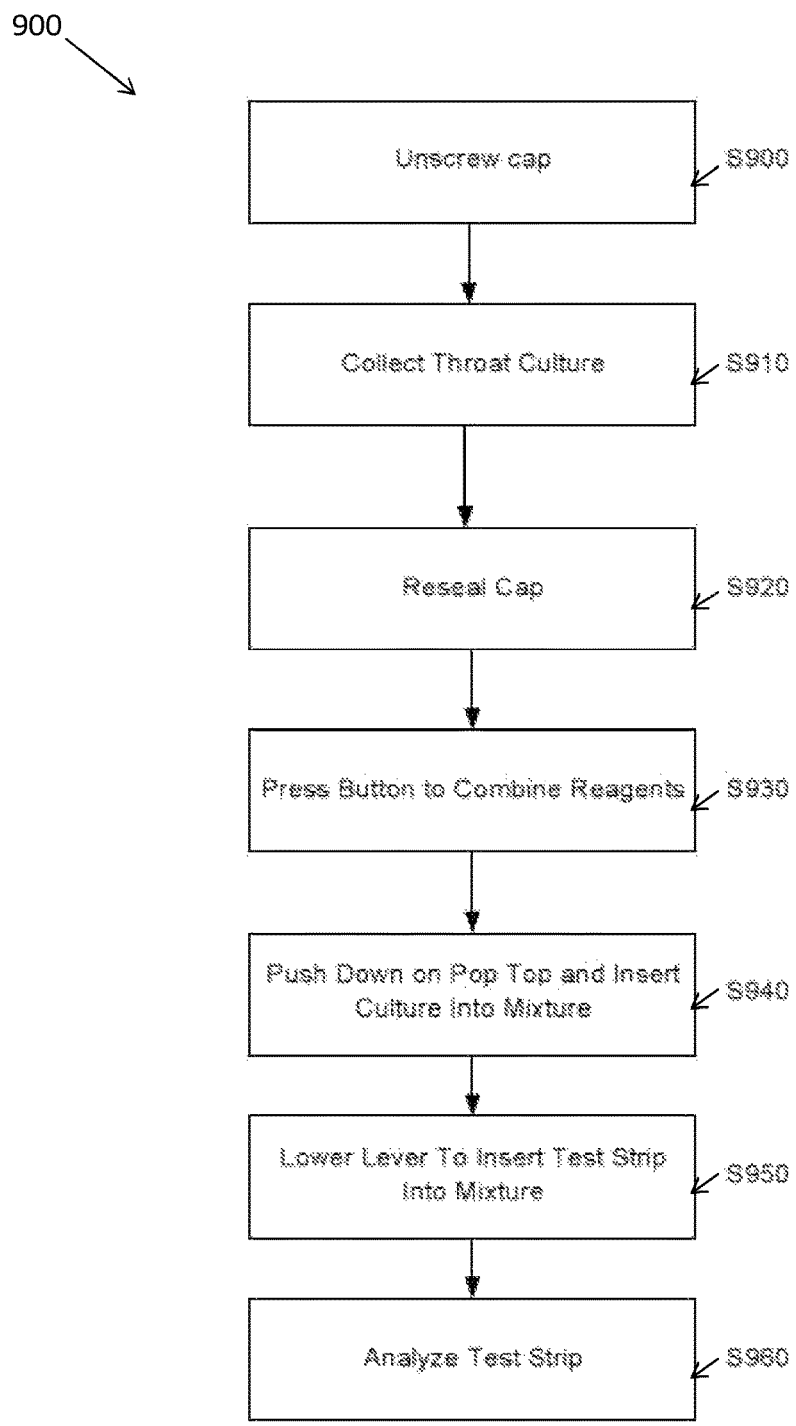
FIG. 9 depicts a flow diagram of an embodiment utilizing a self-contained screening test.

FIG. 9 depicts a flow diagram of an embodiment of a diagnostic test method 900, which can be used with the self-contained screening test 100 described herein.

In a step S900, a tester may untwist a cap disposed on a test tube, wherein coupled to the cap may be a throat swab. For example, the untwisted cap may comprise the dispenser cap 106 of the self-contained test 100, the test tube may comprise the test tube 108, and the throat swab may comprise the throat swab 102.

In a step S910, using the cap with the coupled throat swab a tester may collect a throat swab culture from the throat of a tester. In a further example embodiment, the tester may utilize a tongue depressor, such as the removable tongue depressor 110 of the self-contained test 100, when collecting the throat swab culture.

In a step S920, the tester may re-seal the cap with the throat culture in the test chamber, such as tube 108.

In a step S930, using a button at the bottom of the testing chamber, for example button 130 of the self-contained test 100, the tester may pinch reagents capsules, such as capsules 118 and 120, to puncture barriers between them and between the capsules and the test tube to form a mixture. A first reagent chamber may include sodium nitrate while a second reagent chamber may include acetic acid, and when the reagents are mixed the solution may change colors. In many embodiments, the user may remove a divider separating the reagent chambers from the rest of the test tube by pulling out a lever that otherwise separates the reagent chambers from the rest of the test tube.

In a step S940, the tester may push down on a rubber pop top, for example the collapsible pop top 104 of the self-contained test 100, coupled to the throat swab to insert the throat swab culture into the mixture. This locks the test chamber. The tester may then swirl the mixture to coat the throat swab, such as swab 102, with the mixture.

In a step S950, the tester may dispose a test strip, for example the test strip 124 of the self-contained test 100, into the mixture by applying force or pressure to a lever connected to the test strip. More specifically, the test strip may traverse a rubber seal entry, entering the testing chamber without allowing fluids such as the mixture from exiting the testing chamber. In an embodiment, it may be required or recommended for the mixture to stand for a time threshold, such as a minute, before disposing the test strip into the mixture.

In a step S960, a reaction may cause a result to be displayed on the test strip. Therefore, the tester may be able to read a visible reaction on the test strip to analyze a result. In an embodiment, it may be required or desired for the tester to analyze the reaction on the test strip five to ten minutes after the test strip is exposed to the throat swab culture and mixture. A positive test response can occur when a reaction between a protein on the surface of strep bacteria and chemical in the test materials exists. Either living or dead strep bacteria may produce a positive reaction. A positive culture may indicate that the user may require antibiotics for treatment. In many embodiments, the test will have a sensitivity of at least 92%, meaning that the test will be positive in at least 92 of 100 patients who are documented to have strep throat via throat culture at the same time. In many embodiments, the test will have a specificity of at least 95%, meaning that the test will be negative in at least 95 of 100 patients who are documented to not have strep throat via throat culture at the same time. In some embodiments, negative swab specimens are sent for culture to confirm the absence of strep bacteria.

Although the above steps show method the method 900 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the diagnostic test method.

The method 900 will be less cumbersome and require fewer steps than many known tests of indications such as strep throat. For example, a known test for strep throat may comprise the following steps:
  (i) Just before testing, add 4 drops of Reagent 1 (pink to light red) and 4 drops of Reagent 2 to the Test Tube. The solution should turn light yellow.
  (ii) Immediately insert patient's throat swab into the Test Tube of pale yellow solution. Rotate the swab 10 times in the tube.

(iii) Let stand 1 minute.

(iv) Express as much liquid as possible from the swab by squeezing the sides of the tube as the swab is withdrawn.

(v) Discard the swab.

(vi) Remove Test Stick from the container. Recap the container immediately.

(vii) Place the Absorbent End of the Test Stick (arrows pointing down) into the extracted sample.

(viii) Read the results in 5 minutes. A positive result may be read as soon as the red Test Line and the red Control line appear. Weak positive results may require 5 minutes.

Figure 15:
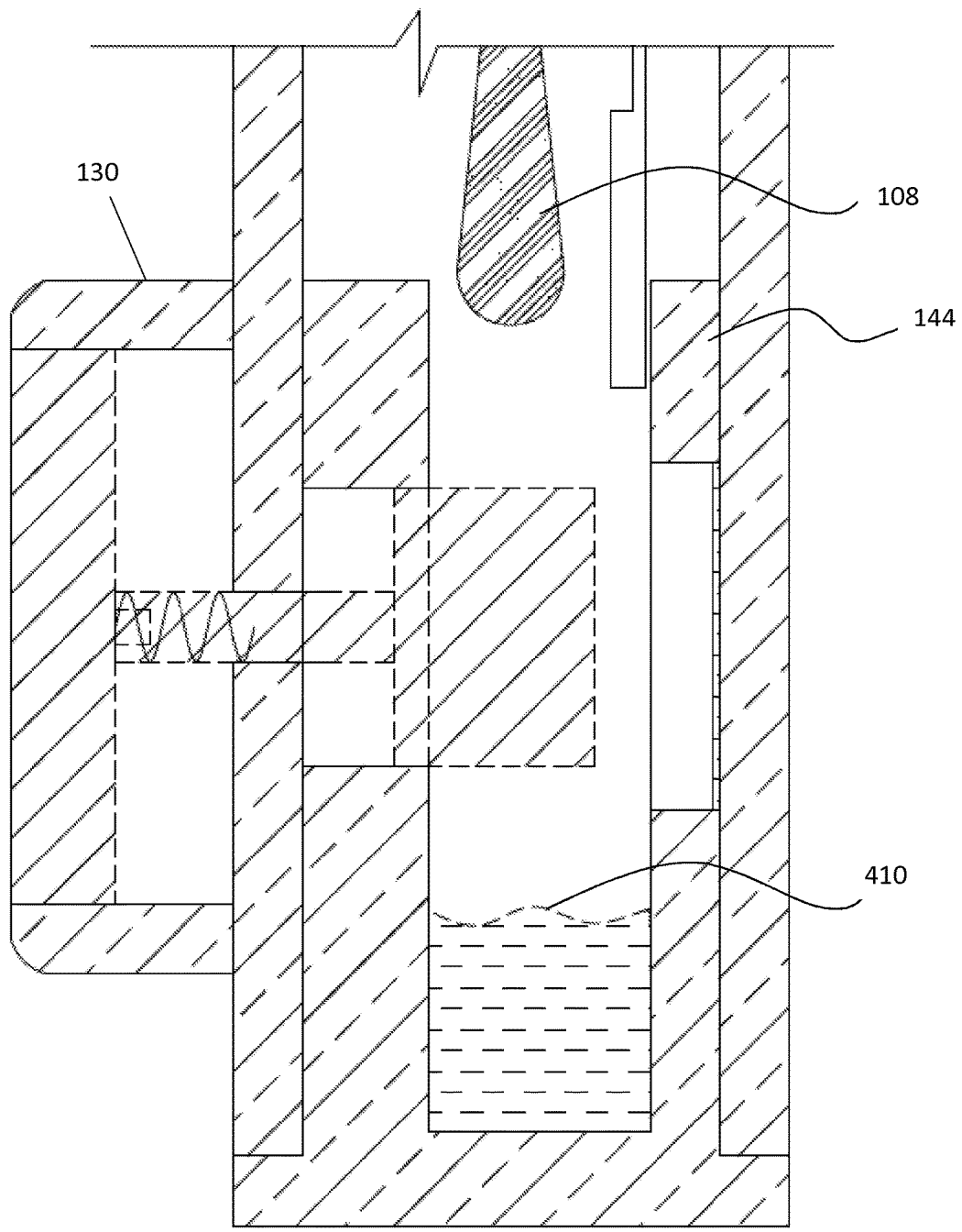
FIG. 15 shows a magnified, section view of the base of the self-contained screening test of FIG. 10 after pressure has been applied to the button to open one or more reagent capsules.
Figure 16:
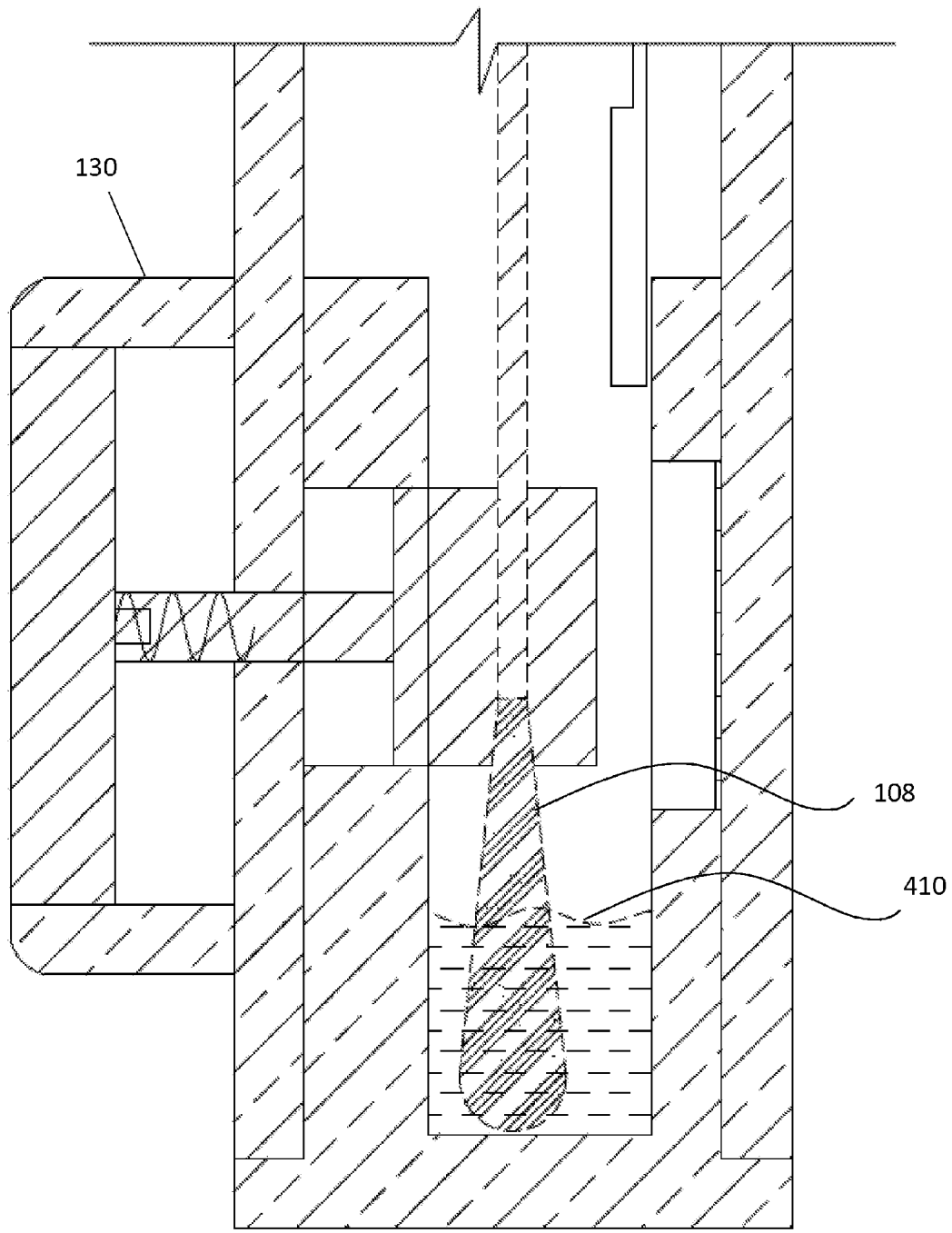
FIG. 16 shows a magnified, section view of the base of the self-contained screening test of FIG. 10 as a test swab is advanced into the sampling portion.
Figure 17:
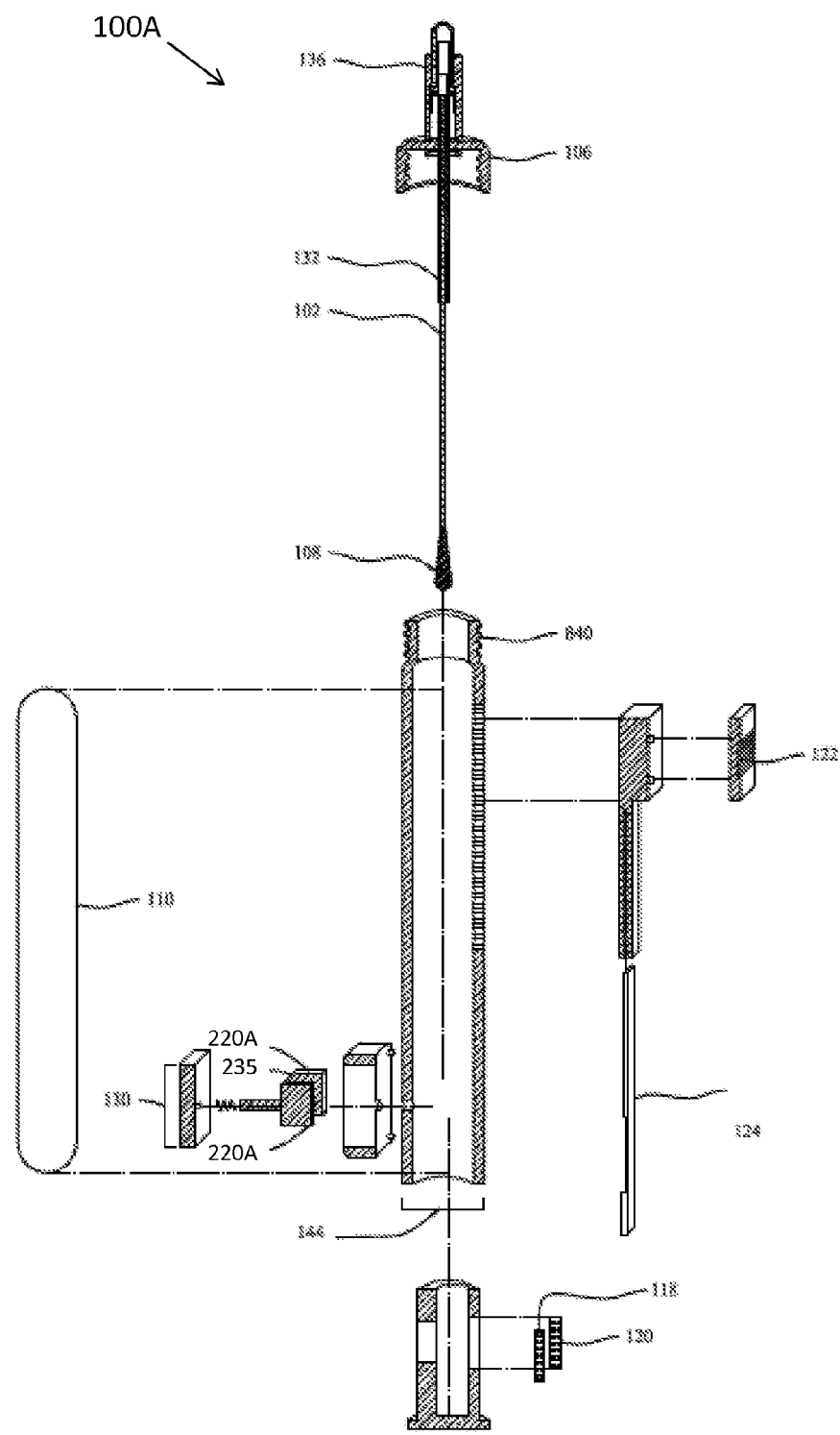
FIG. 17 shows an exploded, sectional view of the self-contained screening test of FIG. 10.
Figure 18:
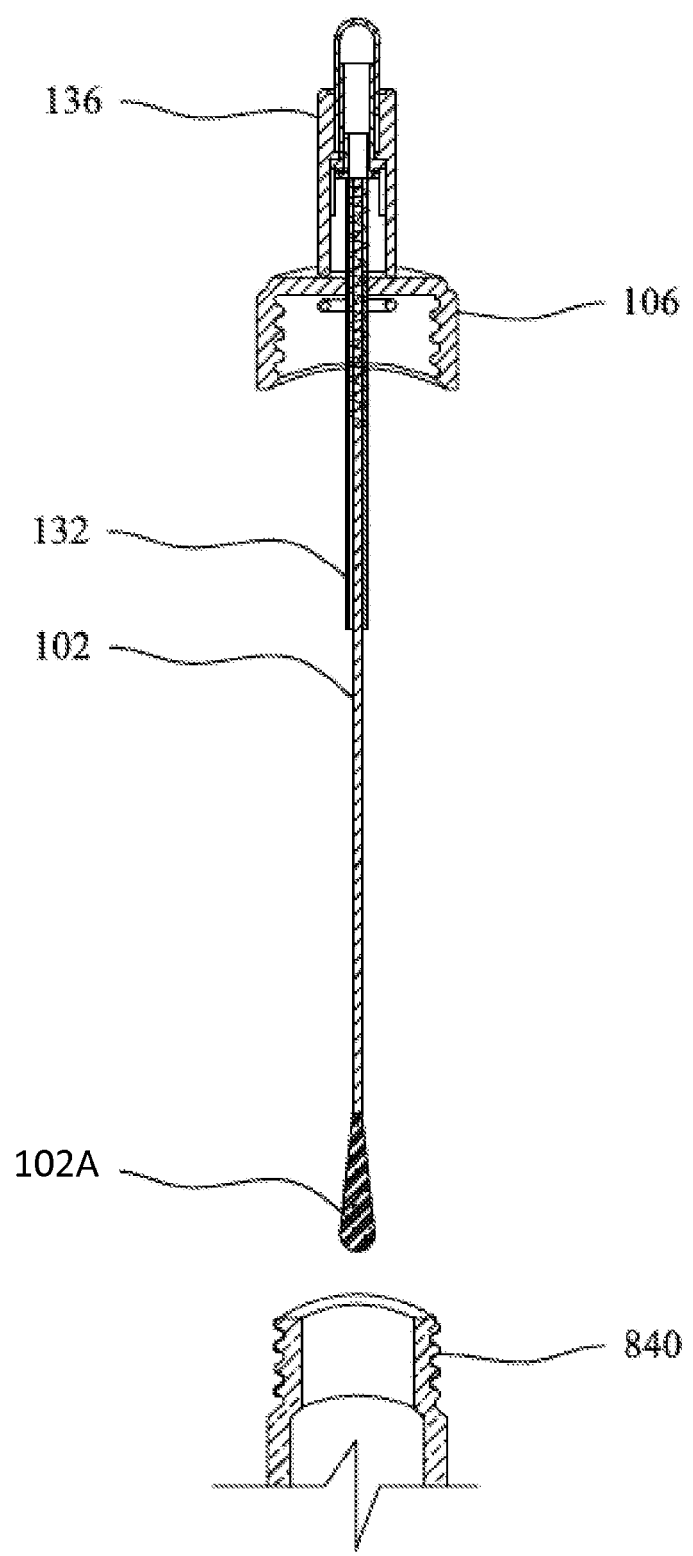
FIG. 18 shows an exploded, section view of the top portion of the self-contained screening test of FIG. 10.
Figure 19:
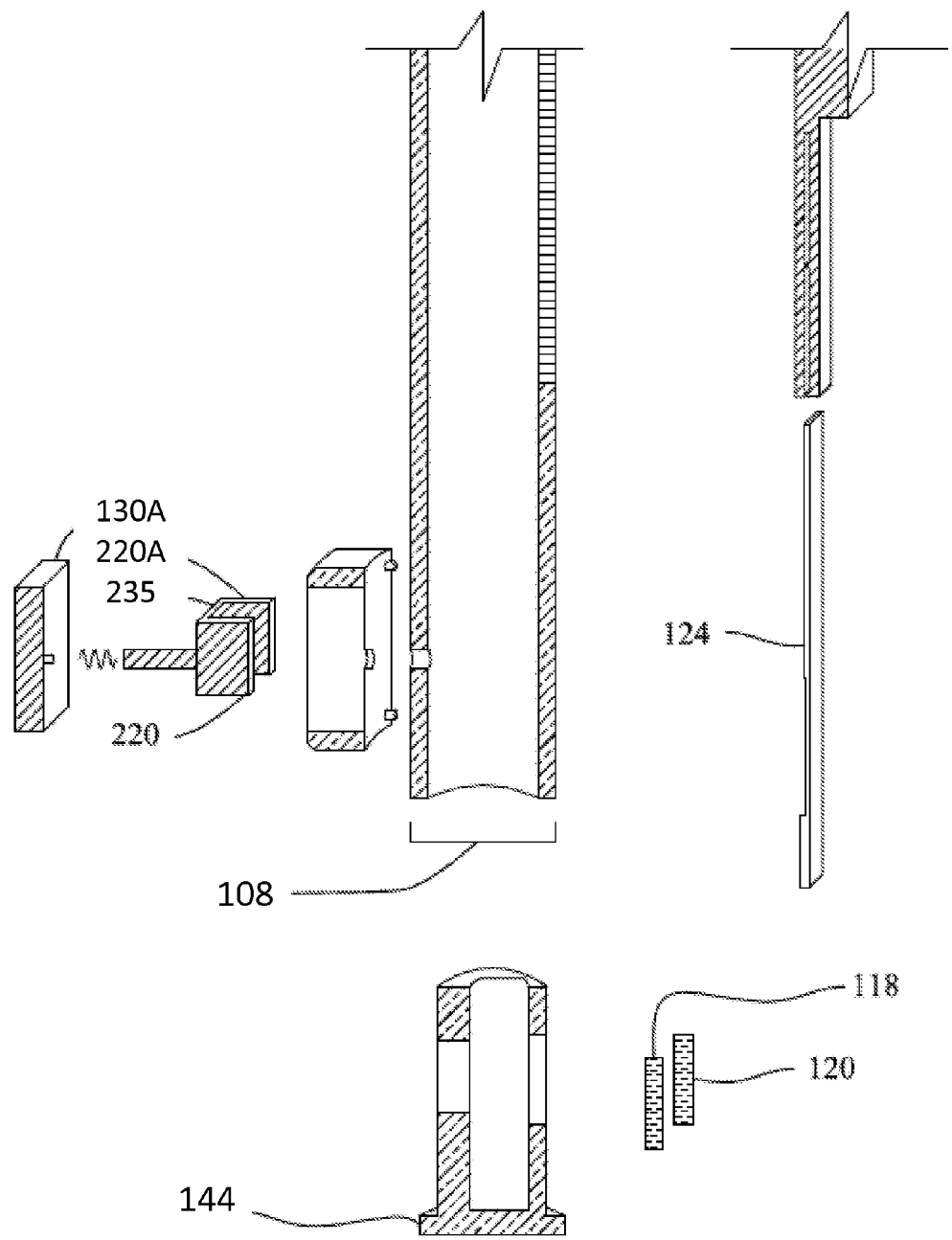
FIG. 19 shows an exploded, section view of the middle and bottom portions of the self-contained screening test of FIG. 10.
Figure 20:
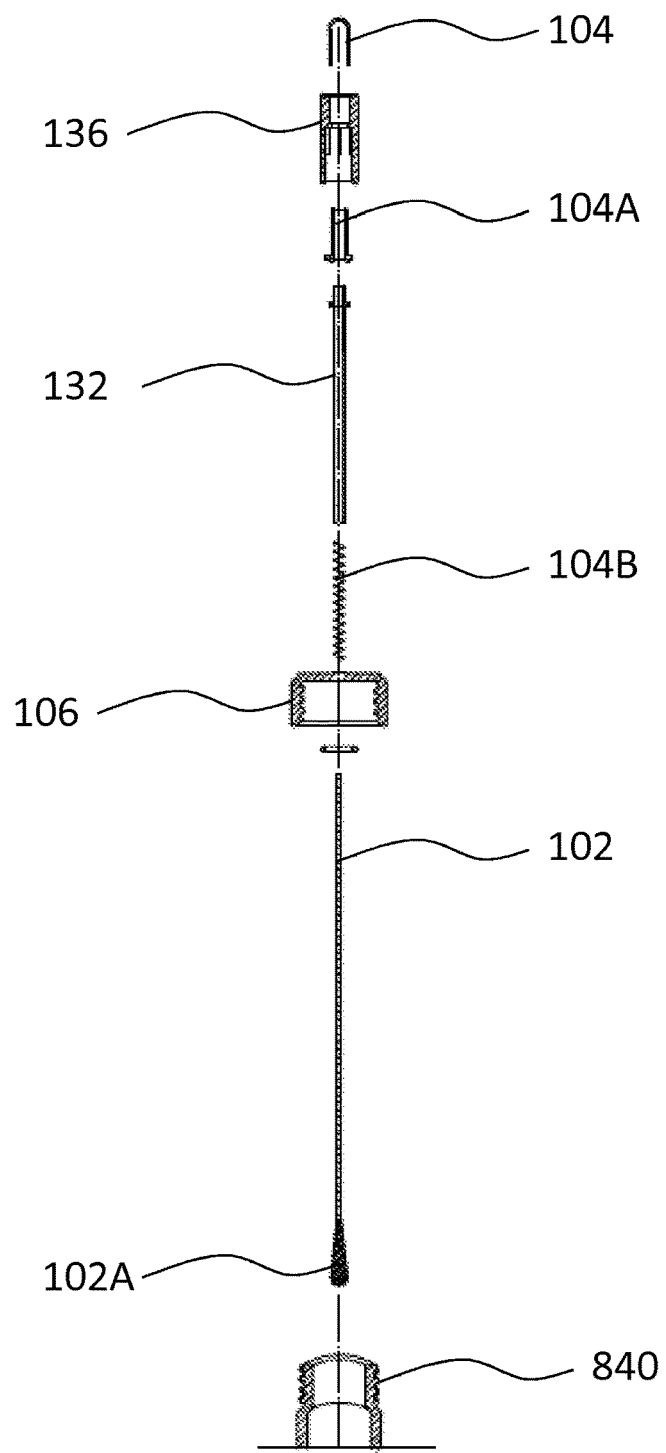
FIG. 20 shows an exploded, section view of the pop top cap of the self-contained screening test of FIG. 10.

Another embodiment of a self-contained screening test is now described. FIGS. 10 to 14 show section views of a self-contained screening test 100A as the test 100A is being used. FIGS. 15 and 16 show section views of the base 144 of the self-contained screening test 100A as a test swab 100A is introduced into a reagent mixture 410. FIG. 17 shows an exploded, section view of the self-contained screening test 100A. FIG. 18 shows an exploded, section view of the top portion of the self-contained screening test 100A. FIG. 19 shows an exploded, section view of the middle and bottom portions of the self-contained screening test 100A. FIG. 20 an exploded, section view the pop top cap of the self-contained screening test 100A.

Figure 10:
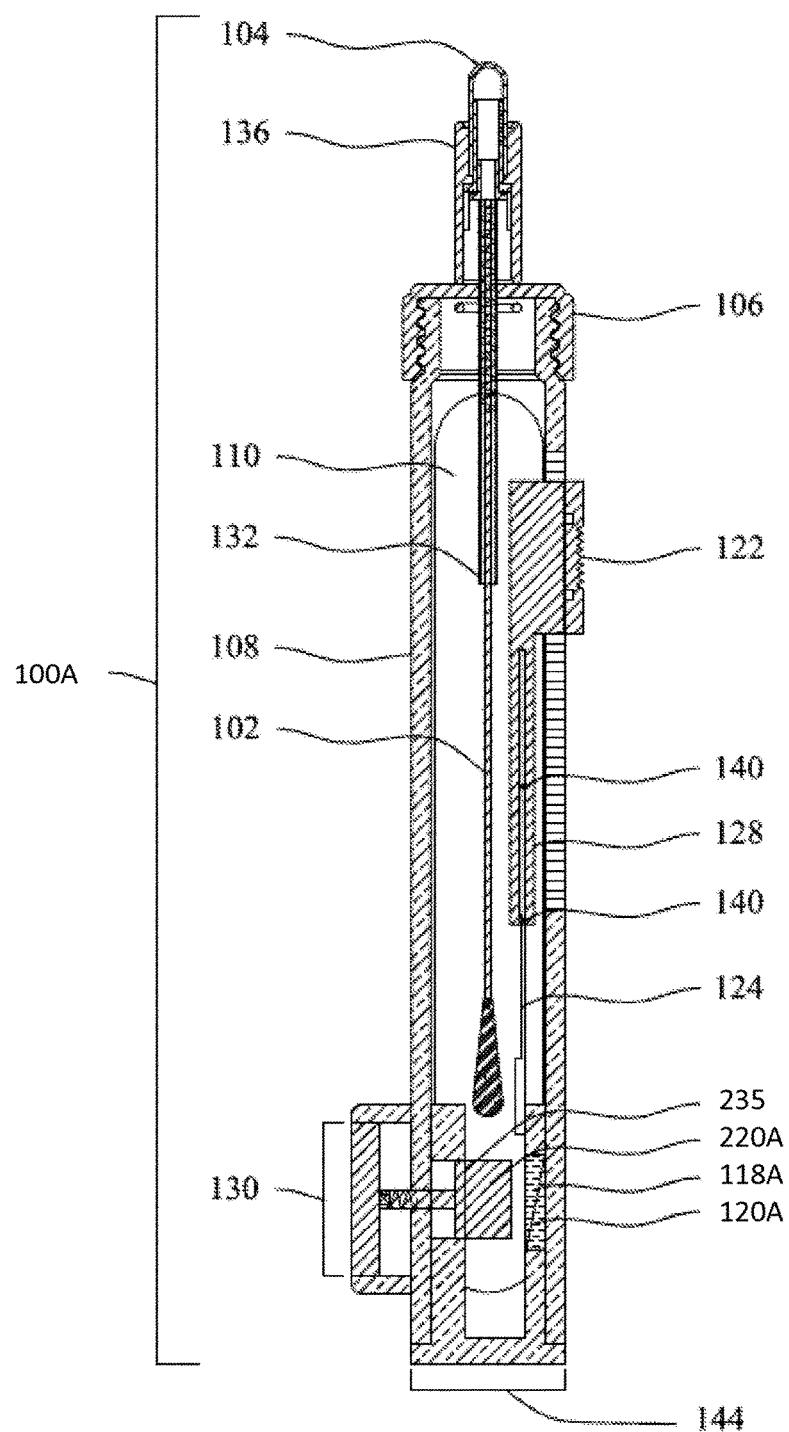
FIG. 10 shows a section view of another embodiment of a self-contained screening test.

FIG. 10 shows a fully assembled self-contained screening test 100A in accordance with many embodiments. The self-contained screening test 100A is generally similar to the self-contained screening test 100 described herein. A difference between the self-contained screening test 100A and the self-contained screening test 100 is the configuration of the reagent capsules (118, 120 for self-contained screening test 100 and 118A, 120A for self-contained screening test 100A).

FIG. 20 shows an exploded, cross-sectional view of top of the self-contained screening apparatus test 100A. FIGS. 17 and 18 show similar views. The self-contained screening test 100A comprises a dispenser cap 106. The dispenser cap 106 comprises a pop top 104, a grip handle 136, and an attachment sleeve 132 for coupling with a swab 102. The pop top 104 may be pressed to engage or disengage, raise or lower the swab 102. The pop top 104 comprises a rigid cylinder 104A and a spring 104B. The travel of the swab 102 can be set by adjusting the stroke to set the height of the final movement of the swab 102. This can be tailored by adjusting the profile of the rigid cylinder 104A. The speed of depression of the swab 102 can be adjusted by changing one or more of the length or diameter of the internal metal spring. The pop top 104 and the dispenser cap 106 may comprise a solid color, opaque polypropylene, ABS plastic or approved equivalent. The swab 102 may be individually wrapped and mounted onto the pop top 104 through attachment sleeve 132.

Referring back to FIG. 10, the self-contained screening test 100A further comprises a main test tube body 108 and a removable tongue depressor 110. The removable tongue depressor 110 may be individually wrapped and adhered to a side of the main test tube body 108. The test tube 108 may comprise a clear polycarbonate or other regulatory agency or otherwise approved material. The tube 108 comprises a threaded mouth 840 as shown in FIGS. 17, 18, and 20, a ridged side for a test strip carrier 128, an opening for a button 130, and can be configured to receive the multi-functional base 144. The test tube body 108 may further comprise one or more horizontal or vertical dividers or guards. The base 144 may be removable from or attached to the test tube body 108. The material of the test tube body 108 may be clear in order to visually check functions as well as read results.

The self-contained screening test 100A further comprises a test strip lever/carrier 122 which can be pressed to advance the test strip 124 into the bottom, testing region of the test tube body 108. The test strip lever/carrier 122 may be made of a solid color, opaque polypropylene. Polypropylene is inherently electrically charged. This charge works to repel fluids, which is beneficial to seal the open, ridged channel in the side of the test tube 100A that acts as a rail for the travel of the test strip lever/carrier 122. The test strip lever/carrier 122 may comprise a two-part assembly comprising an external lever and an internal guard that holds the test strip 124 with locks 140. The external lever and the internal guard may be connected with a minimum of two pin joints that may be friction fit, heat-welded, or solvent welded. In many embodiments, the swab 102 is pre-wrapped so as to create a barrier between the test strip 124 and the test swab 102. In alternative embodiments, a vertical divider may be provided into the test tube 108 to separate the test strip 124 from the test swab 102.

As best shown by FIGS. 17 and 19, the base 144 comprises a void space defined in the cylindrical wall of the base 144 into which the reagent capsules 118A and 120A can be mounted. Opposite the mounting locations for the reagent capsules 118A and 120A are channels for the button projections 220A to travel in order to break the cartridges and release the reagents to mix. The liquid volume of the reagents of reagent capsules 118A and 120A will collect and mix at the bottom of the base 144 in a mixture 410. The base 144 may incorporate a funnel shape to aid in directing kinetic elements to the center. The base 144 may comprise a clear polycarbonate or regulatory agency or otherwise approved equivalent. The base 144 may mate with the test tube 108 with a heat weld, a solvent weld, a threaded connection, or a regulatory agency or otherwise approved equivalent.

In many embodiments, the reagent capsules 118A and 120A are packaged in vacuformed blister packs also known as crush packs, that once broken, lie flat, similar to bubble wrap. One or more of the strength, durability, breakability, and their relations to one another can be tailored by changing the thickness of the packaging material. The capsules 118A and 120A may be made of a clear or translucent plastic, which may incorporate a rough and/or sticky texture that will aid in grip for the friction fit mounting within the pockets in the base 144. The fluids may be sealed within the crush packs 118A, 120A with a durable heat seal. In some embodiments, a vertical divider may further be incorporated into one or more of the base 144 and test tube 108 as an added safety feature. Alternatively or in combination, a label reading "Do Not Use if Seal is Broken" may be incorporated. A divider may comprise a solid removable element or a breakable material such as a thin shatterable polycarbonate film or regulatory agency or otherwise approved equivalent. Poly carbonite film may be beneficial in that it does not produce sharp edges and is biocompatible.

The self-contained test 100A further comprises a button 130 which directs the movement of U-shaped projections 220A which act to (i) break the reagent capsules 118A, 120A and (ii) squeegee the swab 102 once the sample has been submerged in the reagent mixture 410. The button 130 may further comprise a metal spring such that the button 130 can be depressed more than once. The button 130 may be linked with various other components through a pin joint in the shaft of the button 130A. A ridged guard between the button 130 and the test tube body 108 may be incorporated to relieve the pressure that the spring may exert upon the pin joint.

Figure 11:
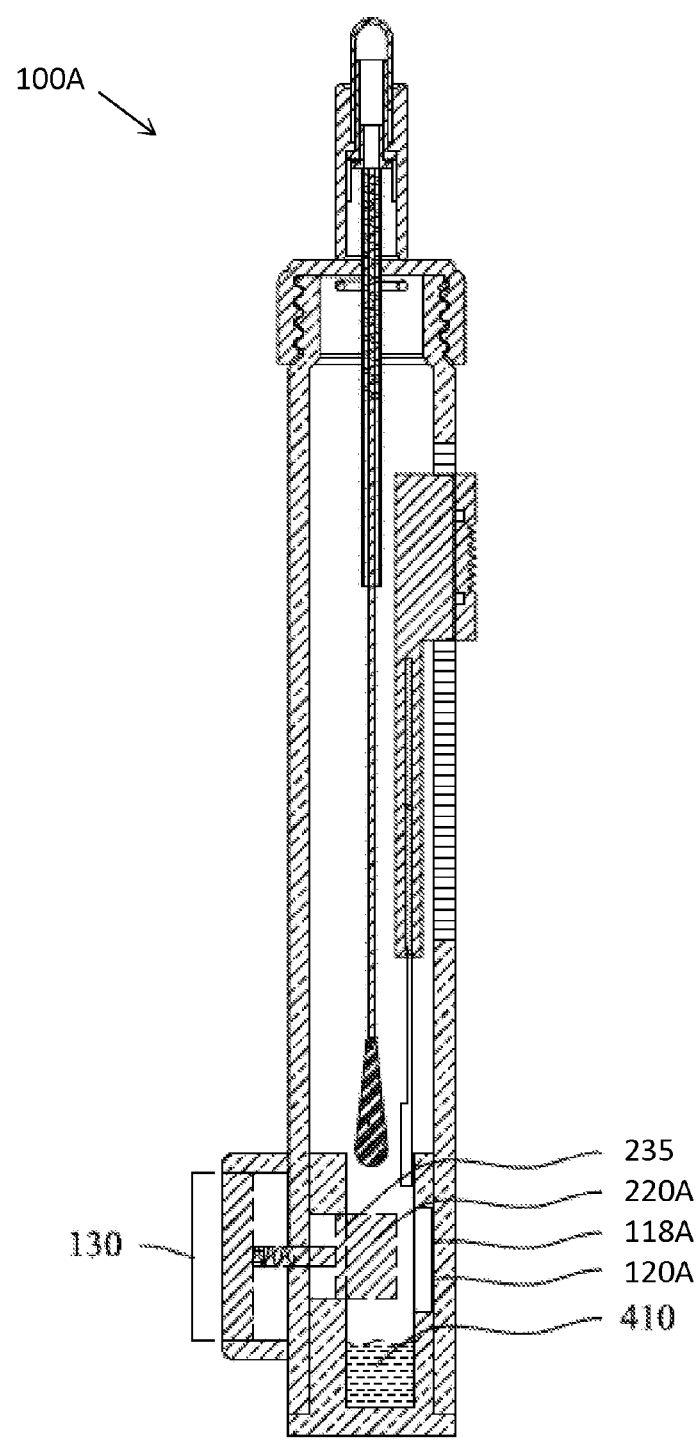
FIG. 11 shows a section view of the self-contained screening test of FIG. 10 after pressure has been applied to a button to open one or more reagent capsules.

As shown in FIG. 11, the button 130 may be depressed to advance the U-shaped projections to break the reagent capsules 118A, 120A. FIG. 15 shows a magnified, cross-sectional view of the base 144 with the reagent capsules 118A, 120A broken to form reagent mixture 410. Once the capsules 118A, 120A are broken, the reagents from within the capsules 118A, 120A will collect and mix at the bottom of the base 144 in a mixture 410. The U-shaped projections 220A direct the force necessary to break the reagent cartridges/blister packs 118A, 120A. The projections 220A may be located in such a way that they also act as a safety that holds the reagent blister packs 118A, 120A in place should they somehow become loose from the friction fit mounting in the base 144.

Figure 12:
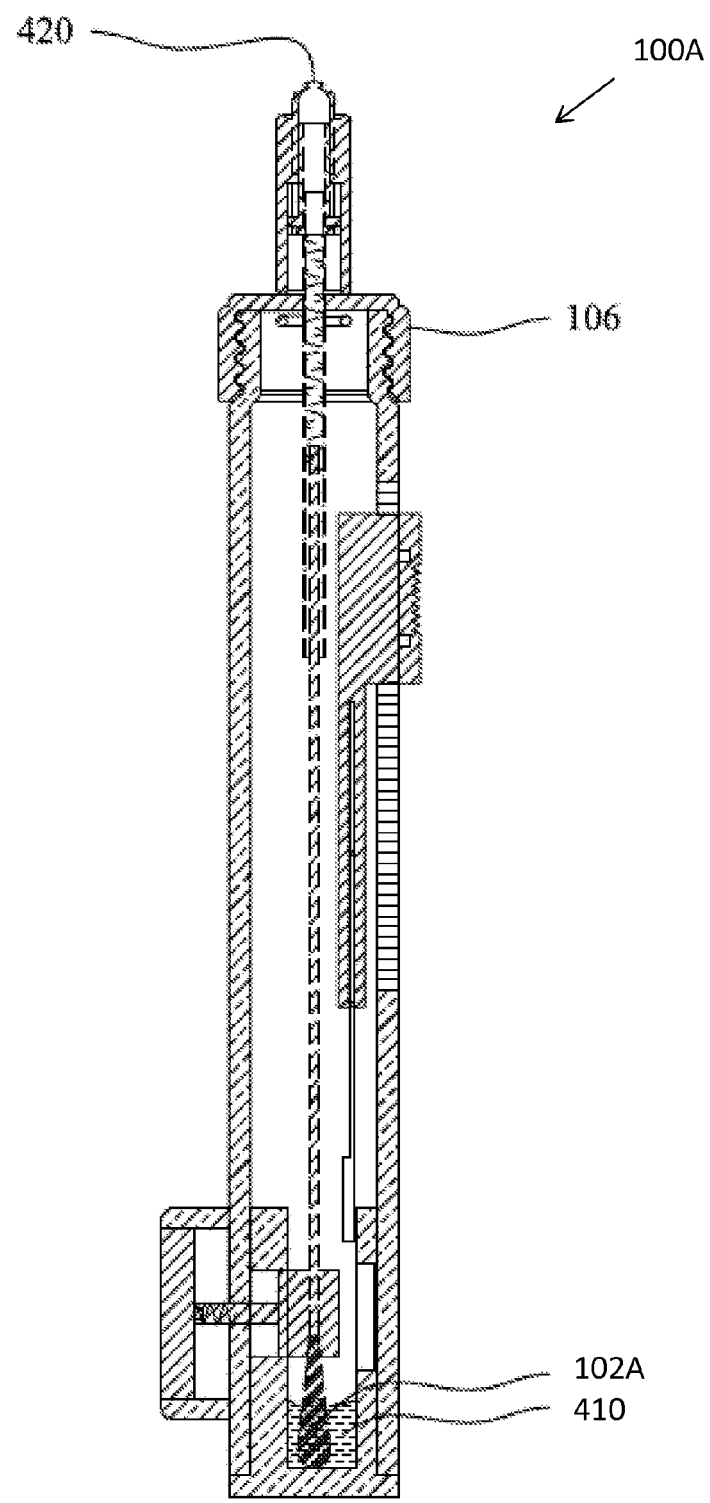
FIG. 12 shows a section view of the self-contained screening test of FIG. 10 as a test swab is advanced into the sampling portion.

As shown in FIG. 12, once the reagent mixture 410 has been formed, the pop top 104 can be depressed to advance the swab tip 102A into the reagent mixture 410. FIG. 16 shows a magnified, cross-sectional view of the base 144 with the swab tip 102A advanced into the reagent mixture 410. Prior to such advancement, the swab 102 may have been removed from the test 100A and used to collect a sample such as from the throat. With the swab tip 102A advanced into the reagent mixture 410, the sample mixes with the reagent mixture 410.

Figure 13:
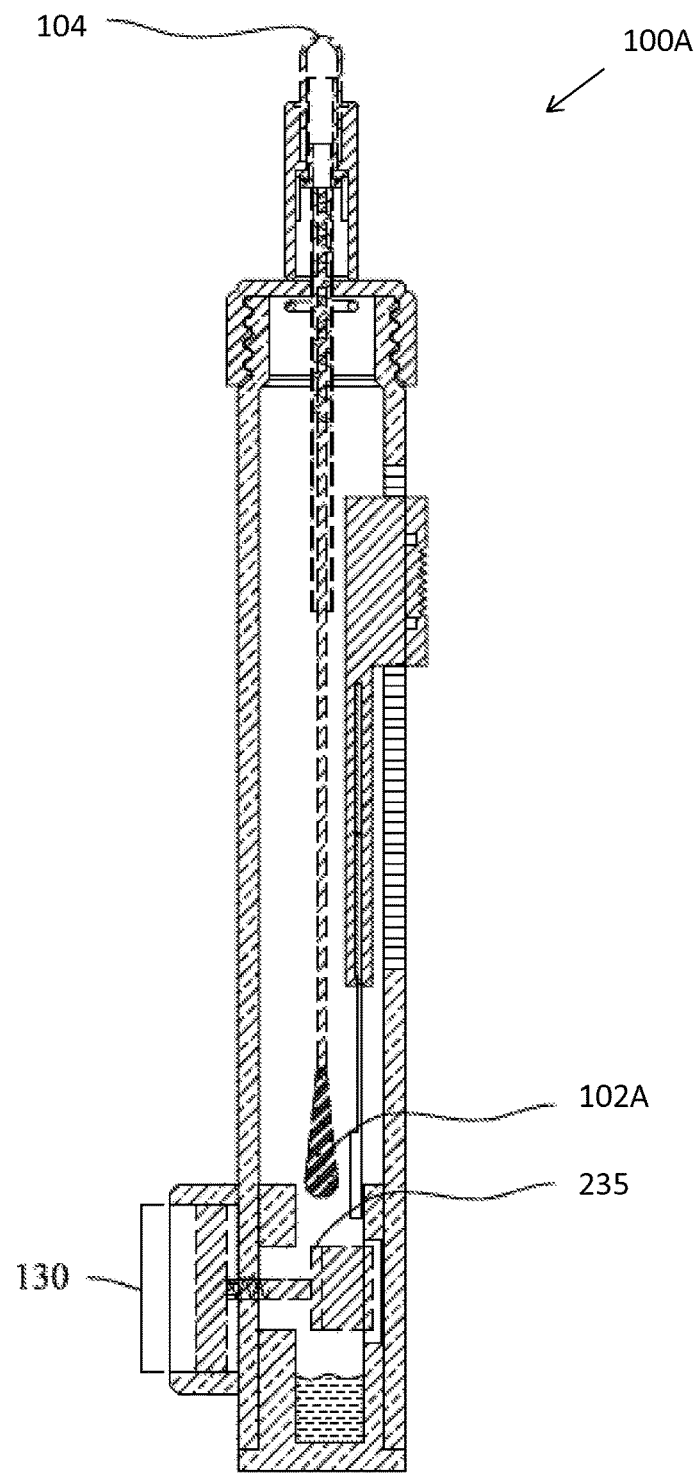
FIG. 13 shows a section view of the self-contained screening test of FIG. 10 after the test swab has been advanced and subsequently retracted.

As shown in FIG. 13, the pop top 104 can be depressed once again to cause the swab 102 to be retracted. As described herein, the U-shaped projection 220A can act as a squeegee to force the remaining sample-reagent mixture from the swab tip 108 as the swab 102 is retracted through the projection 220A.

Figure 14:
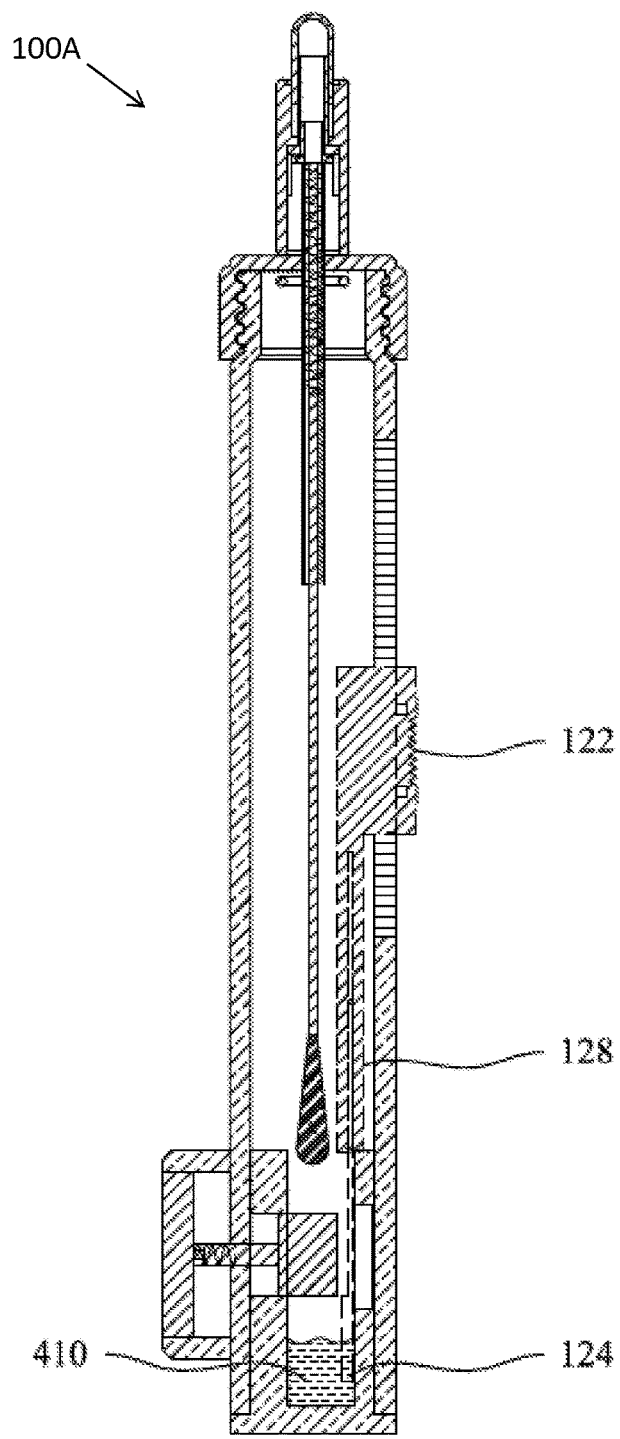
FIG. 14 shows a section view of the self-contained screening test of FIG. 14 after a lever has been pressed to advance a test strip into the sampling portion.

As shown in FIG. 14, the lever 122 can be pressed to advance the test strip 128 into the reagent mixture 410 where the test strip 128 tests for the presence of an analyte.

As described herein, the U-shaped projection 220A can act as a squeegee for the swab tip 102A. This function may correlate with a Strep A Rapid Test Strip Procedure that reads "To remove swab from tube: Press Swab against inside of Tube while removing Swab so most of the liquid stays in the Tube" in an Instruction for Use (IFU) label for example. This step may be key in keeping as much of the sample and small volume of reagent fluids in the mixture 410 present in the base 144 in order to be read by the test strip 124.

The squeegee component of the U-shaped projections 220A is located at the center of the U-shaped projections 220A and is flanked on either side by the part of the projections 220A which break the reagent blister packs 118A, 120A. The button 130 and U-shaped projections 220A, including the squeegee and projections component, may be made of polypropylene. Polypropylene may inherently be electrically charged. This charge can work to repel fluids, which may be beneficial for both the projections part of the U-shaped projections 220A which break the reagent blister packs 118A, 120A, as well as for the squeegee part of the U-shaped projections 220A that will shed the reagent fluids and specimen from the swab tip 102A into the base 144. In addition, this electrical charge will act as a seal for the penetrations that the advanced U-shaped projections 220A create in the side of the test tube 108. In alternative embodiments, such penetrations may be sealed by an O-ring, a one-way valve, a reed valve, or the like.

Figure 21:
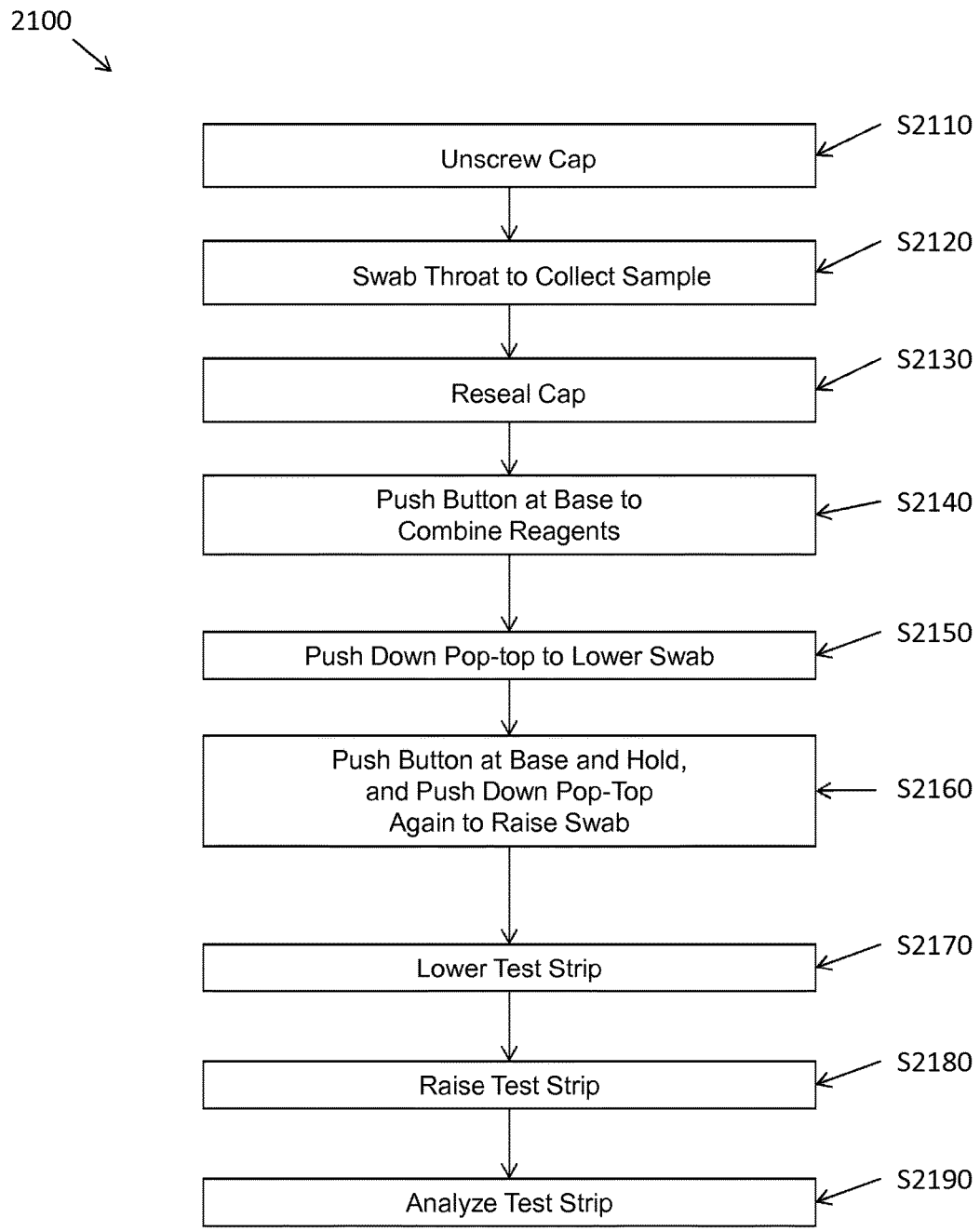
FIG. 21 depicts a flow diagram of a method of using the self-contained screening test of FIG. 10 according to many embodiments.

FIG. 21 depicts a flow diagram of an embodiment of a diagnostic test method 2100 which can be used with the self-contained screening test 100A described herein.

In a step S2110, a tester may untwist a cap disposed on a test tube, wherein coupled to the cap may be a throat swab. For example, the untwisted cap may comprise the dispenser cap 106 of the self-contained test 100A, the test tube may comprise the test tube 108, and the throat swab may comprise the throat swab 102.

In a step S2120, using the cap with the coupled throat swab a tester may collect a throat swab culture from the throat of a tester. In a further example embodiment, the tester may utilize a tongue depressor, such as the removable tongue depressor 110 of the self-contained test 100A, when collecting the throat swab culture.

In a step S2130, the tester may re-seal the cap with the throat culture in the test chamber, such as tube 108 of the self-contained test 100A.

In a step S2140, by pressing a button at the bottom of the testing chamber, for example button 130 of the self-contained test 100A, reagents within the testing chamber can be combined. For example, pressing the button 130 of the self-contained test 100A can break open the reagent capsules 118 and 120 to form a mixture 410 at the bottom of base the 144. A first reagent chamber may include sodium nitrate while a second reagent chamber may include acetic acid, and when the reagents are mixed the solution may change colors.

In a step S2150, the tester may push down on a rubber pop top, for example the collapsible pop top 104 of the self-contained test 100A, coupled to the throat swab to insert the throat swab culture or sample into the mixture. This locks the test chamber. The tester may then swirl the mixture to coat the throat swab, such as swab 102, with the mixture.

In a step S2160, the tester may push the button at the bottom of the testing chamber, for example button 130 of the self-contained test 100A, and hold the button, and push down on the rubber pop top to again raise the swab. For example, by holding the button 130 at the bottom of self-contained test 100A, the projections 220A can be maintained in a position to act as a squeegee for the swab 102 as described herein. Raising the swab 120 can allow the mixture of reagents and sample to pass down to the mixture 410 at the bottom of the base 144.

In a step S2170, the tester may dispose or lower a test strip, for example the test strip 124 of the self-contained test 100A, into the mixture, for example the mixture 410, by applying force or pressure to a lever, for example the lever 122, connected to the test strip. In some embodiments, it may be required or recommended for the mixture to stand for a time threshold, such as a minute, before disposing the test strip into the mixture.

In a step S2180, the tester may raise the test strip, for example the test strip 124 of the self-contained test 100A, from the mixture, for example the mixture 410, by raising the lever connected the lever, for example the lever 122, connected to the test strip.

In a step S2190, a reaction may cause a result to be displayed on the test strip. Therefore, the tester may be able to read a visible reaction on the test strip to analyze a result. In an embodiment, it may be required or desired for the tester to analyze the reaction on the test strip five to ten minutes after the test strip is exposed to the throat swab culture and mixture. A positive test response can occur when a reaction between a protein on the surface of strep bacteria and chemical in the test materials exists. Either living or dead strep bacteria may produce a positive reaction. A positive culture may indicate that the user may require antibiotics for treatment. In many embodiments, the test will have a sensitivity of at least 92%, meaning that the test will be positive in at least 92 of 100 patients who are documented to have strep throat via throat culture at the same time. In many embodiments, the test will have a specificity of at least 95%, meaning that the test will be negative in at least 95 of 100 patients who are documented to not have strep throat via throat culture at the same time. In some embodiments, negative swab specimens are sent for culture to confirm the absence of strep bacteria.

Although the above steps show method the method 900 in accordance with many embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the diagnostic test method.

FIGS. 22 to 32 show various views of a self-contained screening test 100B. The self-contained screening test 100B can comprise many similar features as self-containing screening tests 100 and 100A, particularly self-contained screening test 100A. The same reference numbers in FIGS. 22 to 32 can refer to the same features for self-contained screening tests 100 and 100A described herein. A difference between the screening test 100A and 100B is that the test 100B comprises a base 144A. The base 144A differs from the base 144 in that the pass-through for the button 130 and projections 220 are eliminated. Also, many of the sharp edges at the base 144A are angled to direct components to the center of the base 144A. A ridge has been added to the test tube 108 to act as a stop for the button 130 and projections 220. The exterior of the button housing has been angled to meet ergonomic criteria.

Figure 22:
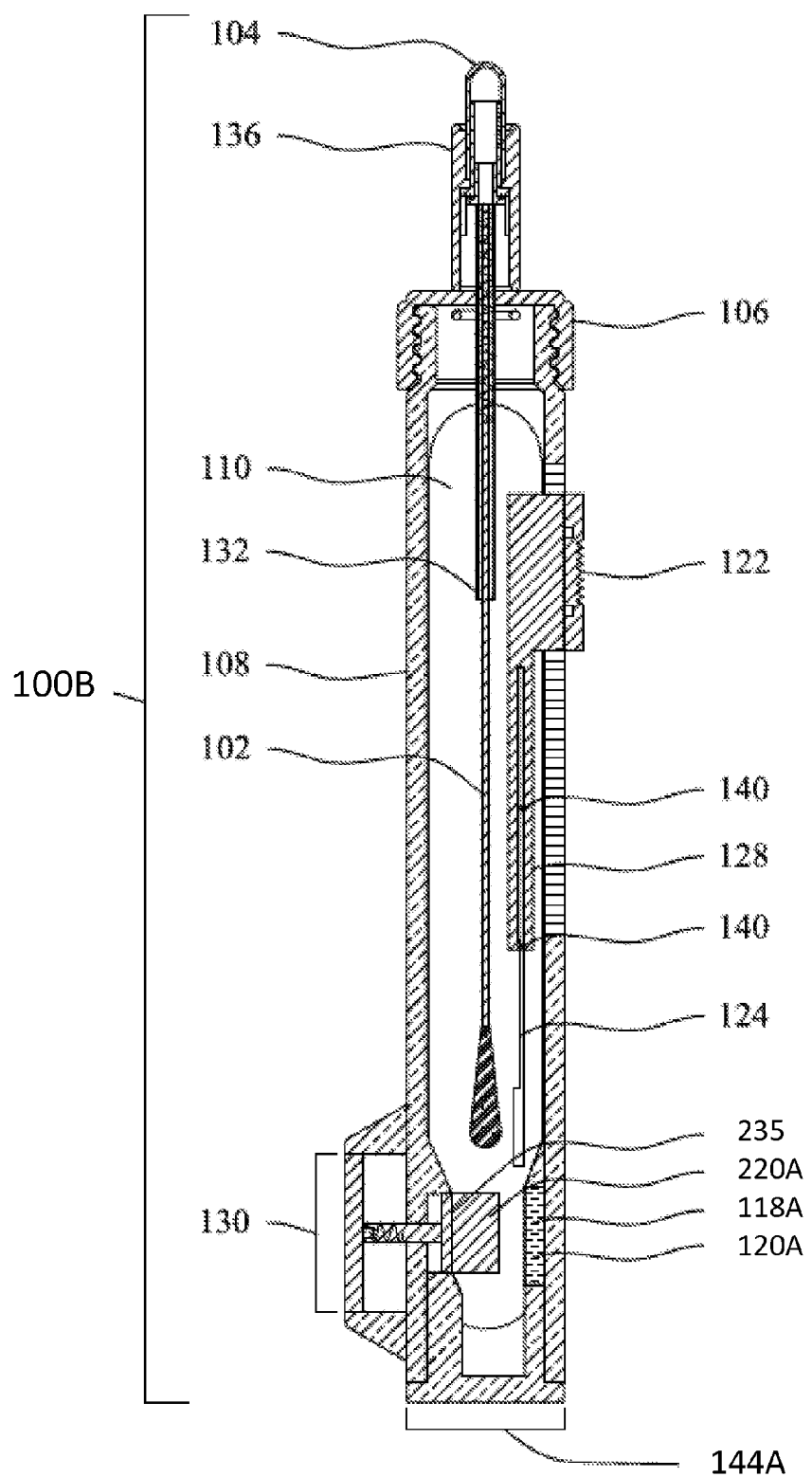
FIG. 22 shows a section view of another embodiment of a self-contained screening test.

FIG. 22 shows a section view of the self-contained screening test 100B.

Figure 23:
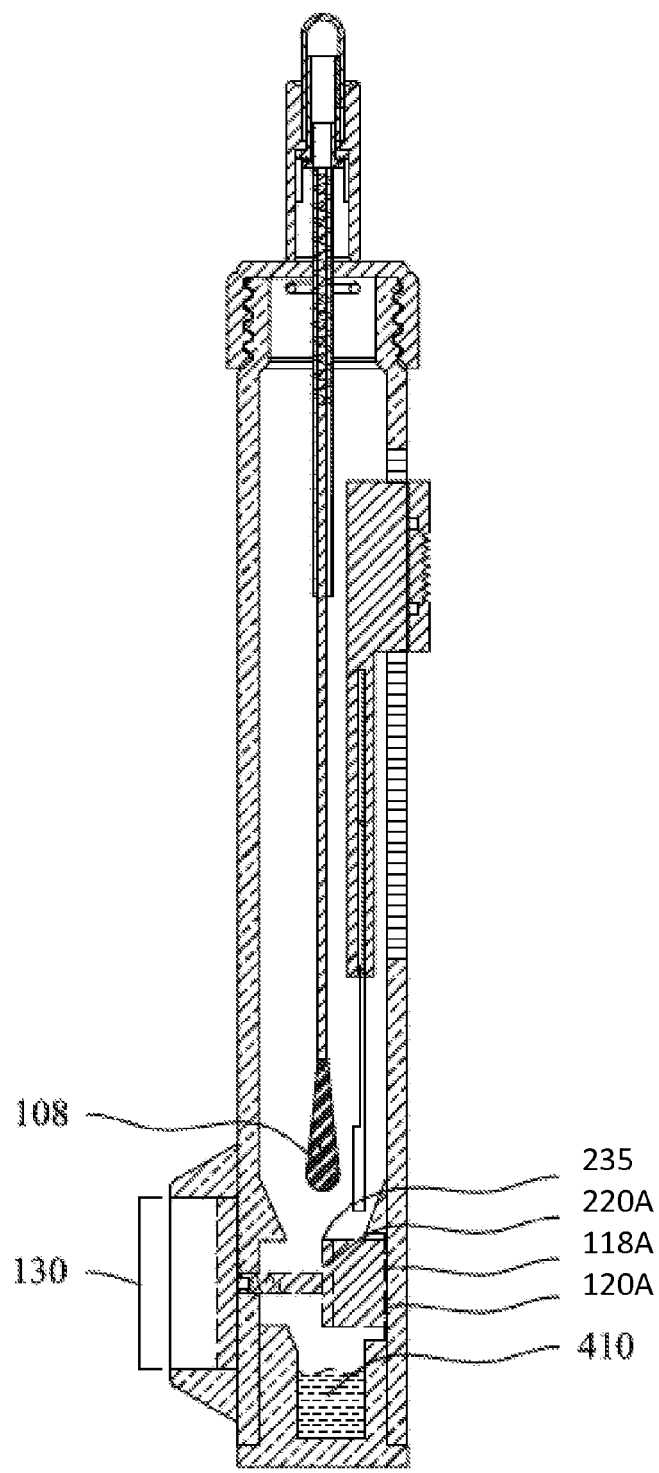
FIG. 23 shows a section view of the self-contained screening test of FIG. 22 after pressure has been applied to a button to open one or more reagent capsules.

FIG. 23 shows a section view of the self-contained screening test 100B after pressure has been applied to the button 130 to open one or more reagent capsules 118, 120.

Figure 24:
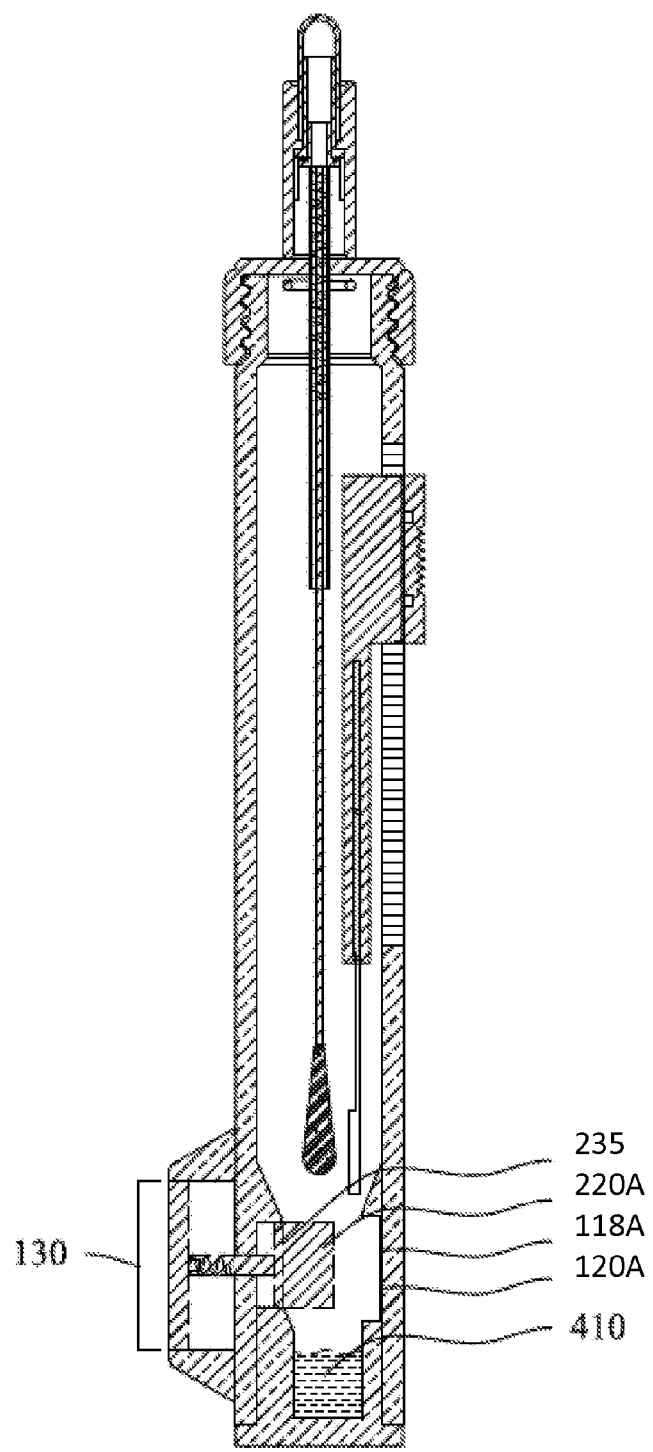
FIG. 24 shows a section view of the self-contained screening test of FIG. 22 after pressure has been applied again to the button to retract the button.

FIG. 24 shows a section view of the self-contained screening test 100B after pressure has been applied again to the button 130 to retract the button 130.

Figure 25:
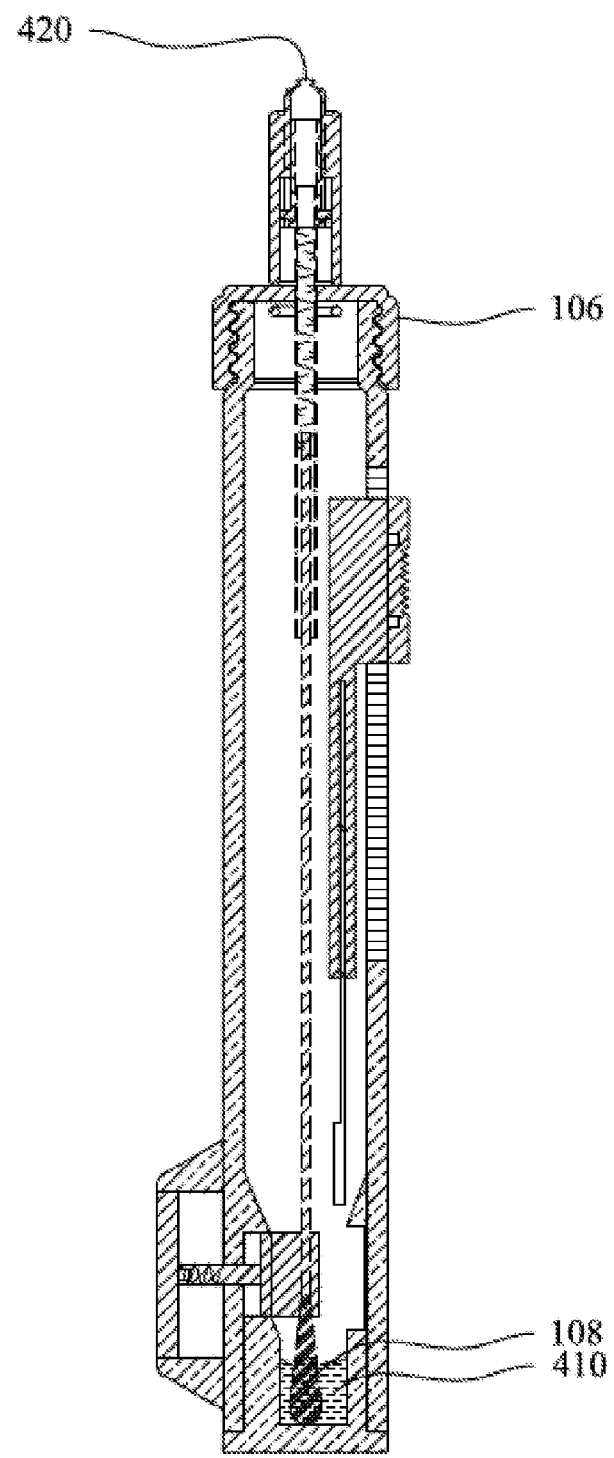
FIG. 25 shows a section view of the self-contained screening test of FIG. 22 after the test swab has been advanced.

FIG. 25 shows a section view of the self-contained screening test 100B after the test swab 102 has been advanced by pressing push top 104 into the collapsed position 420.

Figure 26:
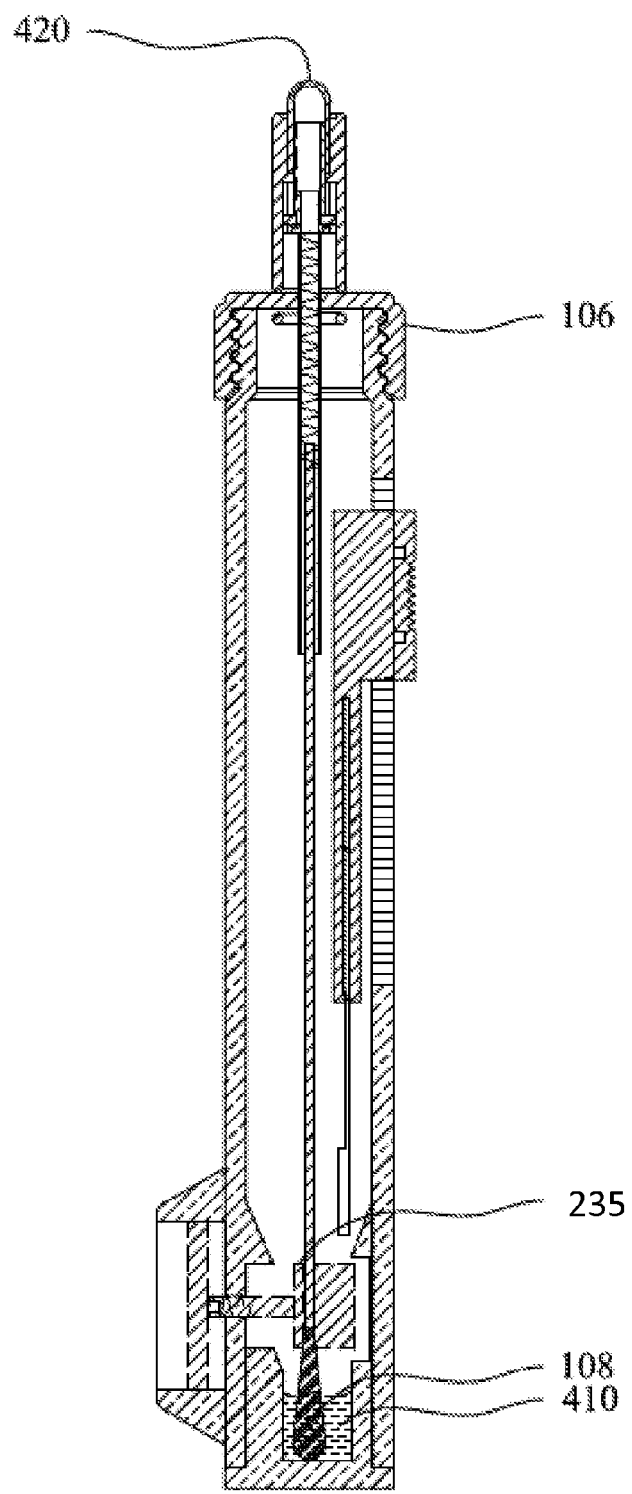
FIG. 26 shows a section view of the self-contained screening test of FIG. 22 after the test swab has been advanced and the button pressed to position a squeegee component.

FIG. 26 shows a section view of the self-contained screening test 100B after the test swab 102 has been advanced and the button 130 pressed to position its squeegee component.

Figure 27:
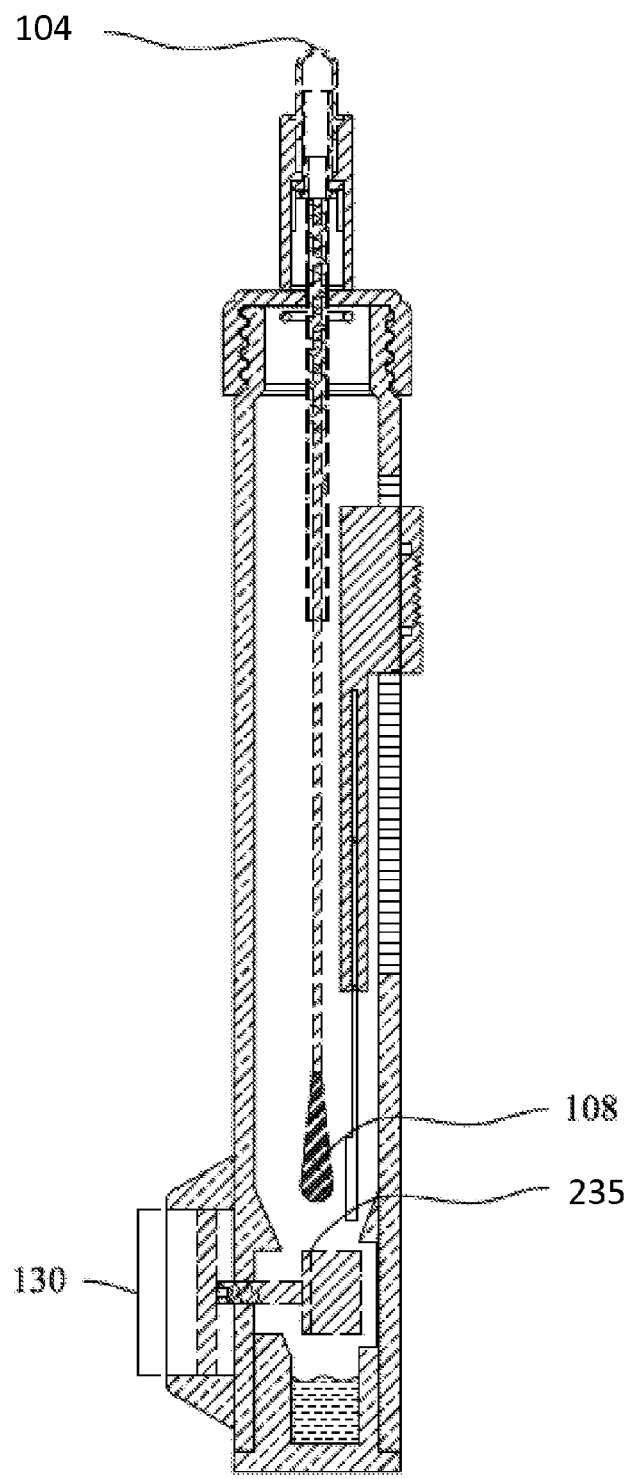
FIG. 27 shows a section view of the self-contained screening test of FIG. 22 after the test swab has been retracted.

FIG. 27 shows a section view of the self-contained screening test 100B after the test swab has been retracted by again pressing push top 104.

Figure 28:
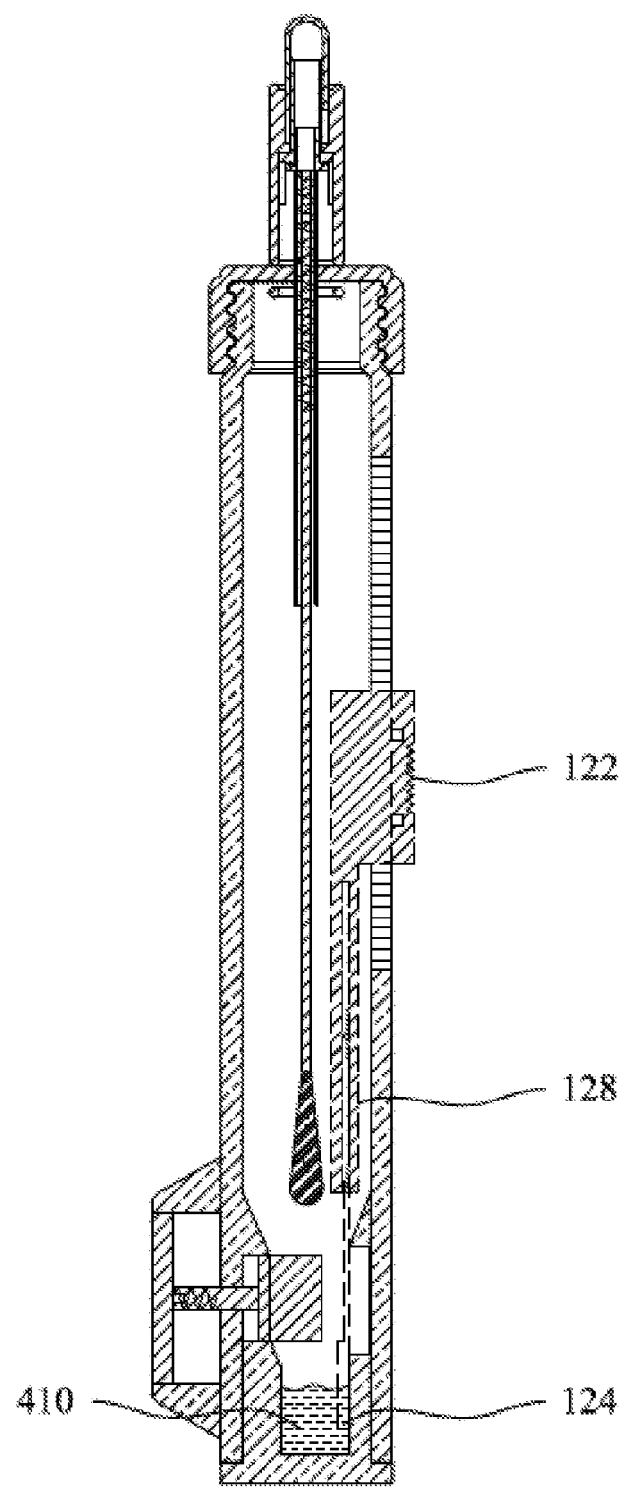
FIG. 28 shows a section view of the self-contained screening test of FIG. 22 after the test strip has been advanced.

FIG. 28 shows a section view of the self-contained screening test 100B after the test strip 124 has been advanced.

Figure 29:
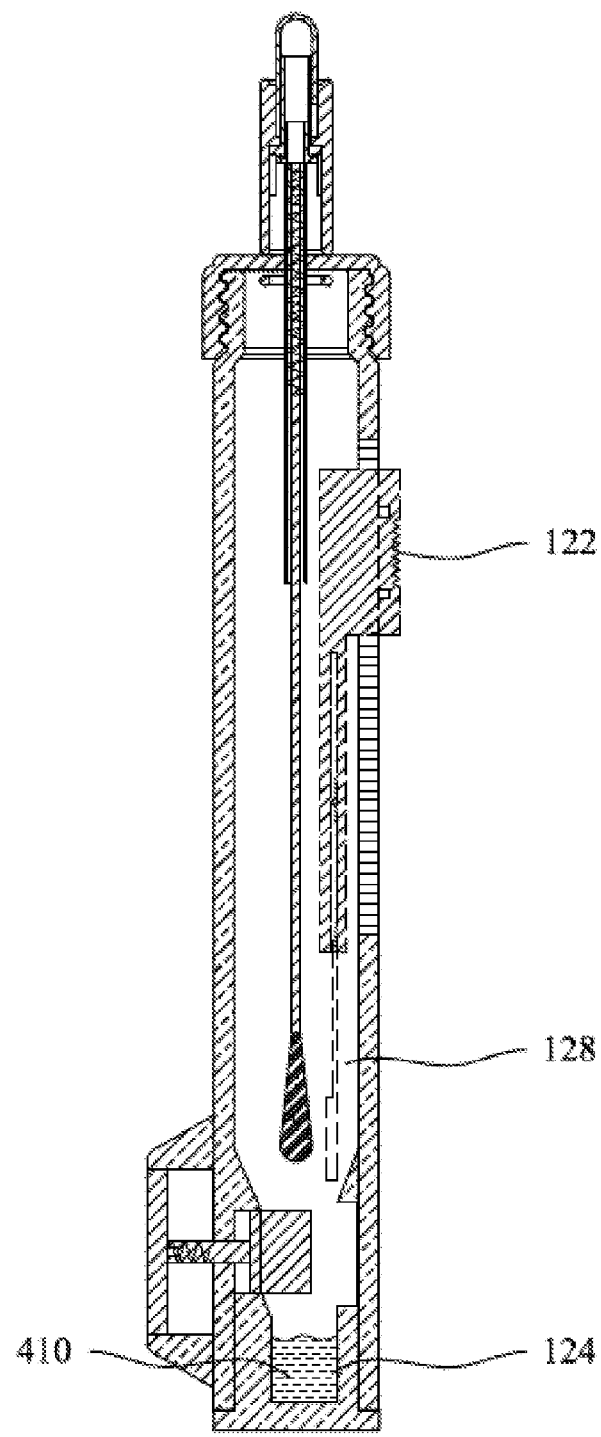
FIG. 29 shows a section view of the self-contained screening test of FIG. 22 after the test strip has been retracted.

FIG. 29 shows a section view of the self-contained screening test 100B after the test strip 124 has been retracted.

Figure 30:
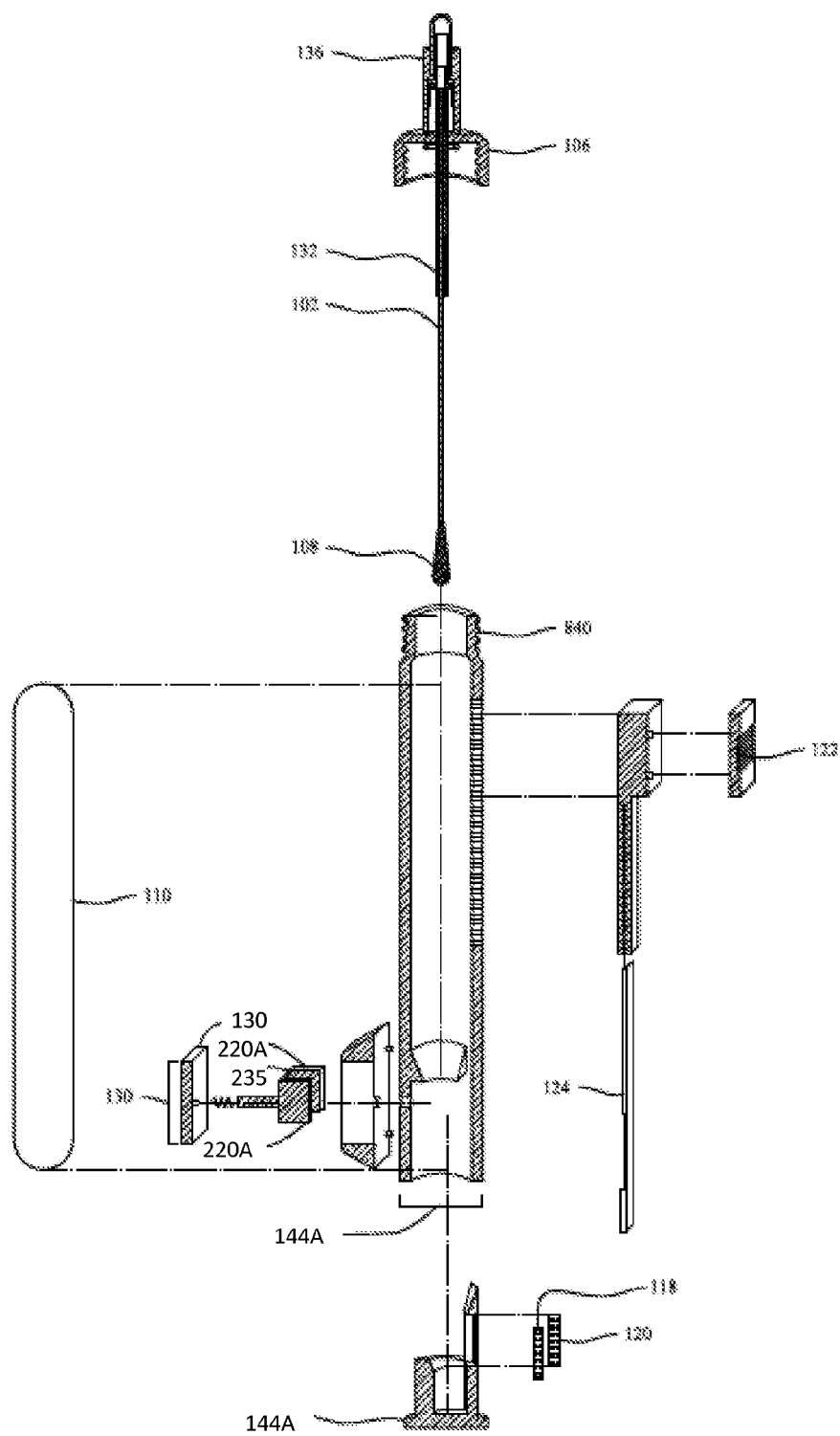
FIG. 30 shows an exploded, section view of the self-contained screening test of FIG. 22.

FIG. 30 shows an exploded, section view of the self-contained screening test of 100B.

Figure 31:
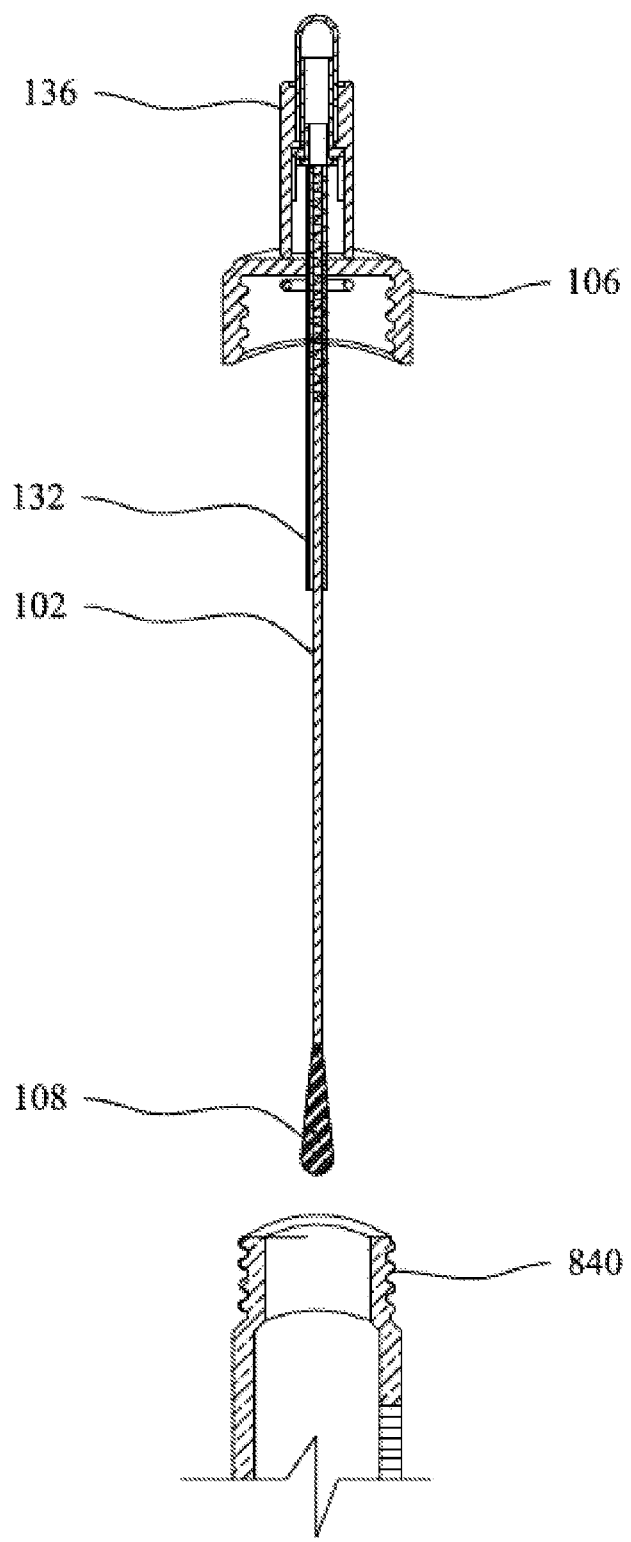
FIG. 31 shows an exploded, section view of the top of the self-contained screening test of FIG. 22.

FIG. 31 shows an exploded, section view of the top of the self-contained screening test 100B.

Figure 32:
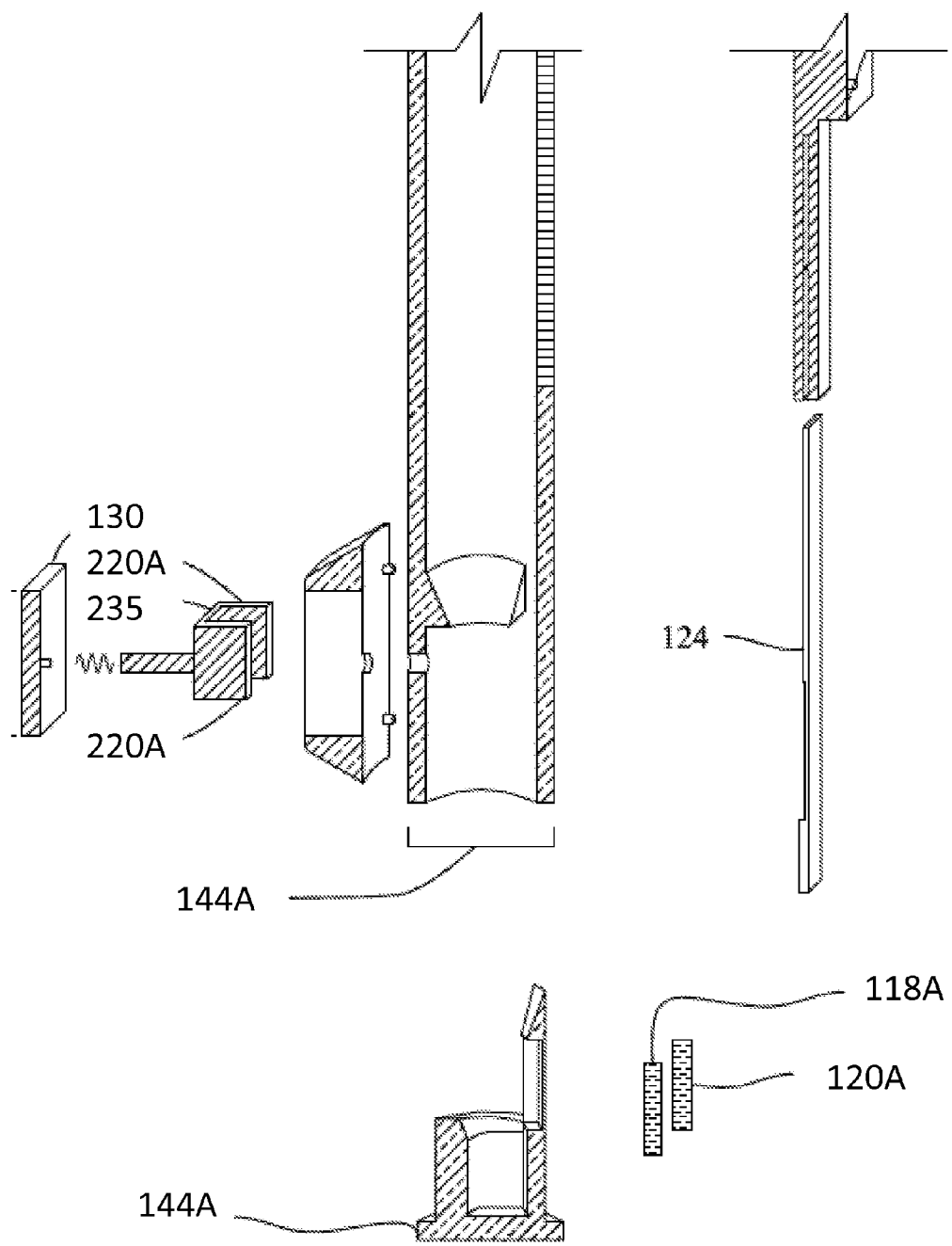
FIG. 32 show an exploded, section view of the bottom of the self-contained screening test of FIG. 22.

FIG. 32 show an exploded, section view of the bottom of the self-contained screening test 100B.

Referring back to the test strip 124 of tests 100, 100A, and 100B, the test strip 124 in many embodiments will typically be used for lateral flow or immunochromatographic strip tests (ICS). Lateral flow tests are often used for the specific qualitative or semi-qualitative detection of many analytes including antigens, antibodies, and even the products of nucleic acid amplification tests. One or several analytes can be tested for simultaneously on the same strip. When used as a clinical diagnostic, urine, saliva, serum, plasma, whole blood, feces, exudates (from wounds or lesions) can all be used as specimens. In environmental or other non-clinical applications, the sample may be derived from soils, dust, vegetation, or food, or environmental swabs such as from food processing plants.

To perform the test, a sample may be placed on the sample pad at one end of the strip. The sample may be used alone as is commonly done with urine or serum compatible tests, or it may be mixed with a buffer specific to the test. This buffer may simply be a diluents/running buffer or it may be much more complex and have specific components or properties required to make the strip perform properly, such as cell lyses buffer. In the following exemplary description, it is assumed that a gold conjugate is being used. While this is one of the most common detection methods, many other detection methods are available and can be used.

With the addition of the sample, the detector molecules are solubilized. When solubilized, the detector molecules mix with and bind to the analyte in the sample (if analyte is present).

Then, capillary action draws the fluid mixture up the sample pad and into the membrane. The sample/detector molecule mix continues to move up the membrane until it reaches the analyte capture molecule. In these lines, a second (and third) antibody or antigen, immobilized as a thin stripe in the nitrocellulose will then capture the complex if it is positive for the target analyte. The control line should show as a visible line, otherwise the test may be invalid and may need to be repeated. If the test is positive, a colored (pink or purple) line develops along with the control line.

Various test operations may be performed.

1. When testing with a strep-A test cassette, the Strep A antigen from the specimen, if any, may react with a colored antibody-colloidal gold conjugate to form Strep A antigen-antibody complexes. The mixture then moves chromatographically across the membrane to the immobilized rabbit anti-strep A antibody at the test band region, and may be captured by the binded antibody, a pink band will thus appear. If there are no antigens in the specimen, no color will emerge on the test line region, which may indicate a negative result.

2. The test performed may be a lateral-flow immunoassay. The test, containing a highly specific and sensitive antibody reactive to the Strep A antigens, may be specific to Group A. To perform the test, a throat swab specimen is collected. The extraction reagents may then be mixed in a tube, which may result in a green color change, and the swab can be added in order for the antigenic component of the bacteria to be extracted. Extraction may occur within one minute, after which the extracted sample is added to the sample well of the test cassette. The extracted sample may migrate by capillary action through a pad consisting of a pink label containing rabbit polyclonal anti-strep A antibody and a blue control label. If the extracted solution contains strep A antigen, the antigen may bind to the antibody coupled to the pink test label which, in turn, will bind a second rabbit polyclonal anti strep A antibody spotted on the membrane, which may result in the formation of a pink-to-purple test line. A blue control line may also appear next to the letter "C" on the test cassette, which may indicate that the reagents were mixed and added properly, that the proper volume of fluid has entered the test cassette, and capillary flow has occurred. A blue control line may appear in a properly functioning test cassette. If strep A is not present or present at very low levels, only a blue control line may be visible. Among the parts and reagents used for the above operations include:
(i) Rabbit polyclonal antibody to strep A (for the test line) and a control rabbit polyclonal antibody capable of binding the blue control label (for the control line);
(ii) Extraction Reagent A;
(iii) 4M Sodium Nitrite;
(iv) Extraction Reagent B;
(v) 0.2M Acetic Acid; and
(vi) Sterile rayon-tipped swabs on solid plastic shafts.

3. The test performed may comprise a qualitative, lateral flow immunoassay for the detection of Strep A carbohydrate antigen in a throat swab such as swab 102. In this test, the antibody specific to Strep A carbohydrate antigen may be coated on the test line region of the strip. During testing, the extracted throat swab specimen may react with antibody specific to Strep A carbohydrate that is coated onto particles. The mixture can migrate along the membrane. If the Group A *Streptococcus* antigen is present in the sample, it may form a complex with the anti-Group A *Streptococcus* antibody conjugated color particles. The complex may then be bound by the anti-Group A *Streptococcus* capture antibody and a visible red Test Line will appear to indicate a positive result. To serve as a procedural control, a red line may appear in the control region if the test has been performed properly. If a red line does not appear in the control region, the test result may be invalid. The reagents used for this test may include:
(i) for the positive control, nonviable group A Streptococci and 0.1% sodium azide;
(ii) for the negative control, nonviable group C Streptococci and 0.1% sodium azide;
(iii) for reagent 1, 2M sodium nitrite; and
(iv) for reagent 2, 0.3M acetic acid.

These various test operations may be validated. The tests may have a sensitivity of at least 95%, which may be high enough to be used reliably in a point of care setting without a back-up culture. Tests with a low rate of false negatives may lead to a very low risk of complications from infections.

Experimental Section

A prototype self-contained test was prepared and tested. The prototype self-contained test comprises the following parts with the below described properties and attributes.

Test Tube:
Material: Polycarbonate Tube Rigid (CAS number 25971-63-5 base polymer)
Color: Clear
Hardness: Rockwell R 73-78
Temperature Range: −275° F. to 250° F.
Melt point 300° F.+/−5° F.
Inside Diameter: ¾"+/−0.015"
Outside Diameter: 1"+/−0.015"
Length: 6⅞"+0.000/−0.063"
Push Button Hole: ⅛"+/−0.010"
Threaded Top: 24M-420+/−0.010"
(CMA/SPI thread specification for plastic enclosures translates to: 24 mm outer diameter, 23 mm inner diameter, 0.4" long, 2 threads)
Test Strip Holder Track
Length: 3"+/−0.010"
Outer Width: 3/16"+/−0.010"
Inside Width: ⅛"+/−0.010"
Tooth Spacing: 1/16"+/−0.010"
Tooth Length: 1/16"+/−0.010"
Tooth Width: 1/32"+/−0.010"

Reagent Cartridge:
Material: Polycarbonate Cast (CAS number 25971-63-5 base polymer)
Color: Clear
Hardness: Rockwell R 73-78
Temperature Range: −275° F. to 250° F.
Melt point 300° F.+/−5° F.
Outer Diameter: ¾"+/−0.015"
Height: 1.70"+/−0.010"
Inner Cavity
Diameter 0.300"+/−0.001"
Length: 0.550"+/−0.001"
Push Button Housing:
Material: Polycarbonate (CAS number 25971-63-5 base polymer)
Color: Clear
Hardness: Rockwell R 73-78
Temperature Range: −275° F. to 250° F.
Melt point 300° F.+/−5° F.
Outer Height: 1¼"+/−0.010"
Inner Height: 1"+/−0.010"
Outer Width: ¾"+/−0.010"
Inner Width: ½"+/−0.010"
Thickness: Varies 0.5693" to 0.3945"+/−0.010"
Cap:
Material: Polypropylene (CAS number 9003-07-0)
Form: Pellet (to be melted and cast)
Color: Red
Hardness: Rockwell R 92-98
Temperature Range: −250° F. to 300° F.
Melt point 325° F.+/−5° F.
Density: 0.855 g/cm$^3$ amorphous
Outside Diameter: 1⅛"+/−0.015"
Inner Diameter: 1"+/−0.015"
Height: ⅝"+/−0.010"
Internal Thread: 24M-420+/−0.010"
Hole for Push Button: 3/16"+/−0.010"
External Ridges (8 equally spaced at 45° apart radially)
Length: 9/16"+/−0.010"
Diameter: ⅛"+/−0.010"
***If a liner has to be added for sealing purposes it should be Polyethylene F217
Test Strip Holder:
Material: Polypropylene (CAS number 9003-07-0)
Form: Pellet (to be melted and cast)
Color: Red
Hardness: Rockwell R 92-98
Temperature Range: −250° F. to 300° F.
Melt point 325° F.+/−5° F.
Density: 0.855 g/cm$^3$ amorphous
Length: 2 15/16"+/−0.010"
Width: 3/16"+/−0.010"
Thickness: 5/32"+/−0.010"
Test Strip Button
Length: 1"+/−0.010"
Width: 5/16"+/−0.010"
Thickness: ⅛"+/−0.010"
Push Button:
Material: Polypropylene (CAS number 9003-07-0)
Form: Pellet (to be melted and cast)
Color: Red
Hardness: Rockwell R 92-98
Temperature Range: −250° F. to 300° F.
Melt point 325° F.+/−5° F.
Density: 0.855 g/cm$^3$ amorphous
Button:
Length: 1"+/−0.010"

Width: ½"+/−0.010"
Thickness: ³⁄₁₆"+/−0.010"
Arm:
Length: ½"+/−0.010"
Diameter: ⅛"+/−0.001"
Capsule Break Arm:
Length: 0.363"+/−0.001"
Outer Width: ⅜"+/−0.010"
Inner Width: ¼"+/−0.010"
Height: ½"+/−0.010"
Pop Cap:
Material: Polypropylene (CAS number 9003-07-0)
Form: Pellet (to be melted and cast)
Color: Sea Green
Hardness: Rockwell R 92-98
Temperature Range: −250° F. to 300° F.
Melt point 325° F.+/−5° F.
Density: 0.855 g/cm$^3$ amorphous
Length: 3⅛"+/−0.010"
Diameters: ⅜", ⁵⁄₁₆", ⅛" all +/−0.010"
Push Button Spring:
Material: 301 Spring Tempered Stainless Steel
Yield Strength: 1014 MPa
Hardness: Rockwell 42 (maximum)
Push Button Spring
Length: ½"+/−0.100"
Diameter: ³⁄₁₆"+/−0.010"
Wire Diameter: ¹⁄₆₄"+/−0.001"
Pop Cap Spring:
Material: 301 Spring Tempered Stainless Steel
Yield Strength: 1014 MPa
Hardness: Rockwell 42 (maximum)
Length: 1"+/−0.100"
Diameter: ³⁄₁₆"+/−0.010"
Wire Diameter: ¹⁄₆₄"+/−0.001"
Blister Pack (2):
Material: Polycarbonate Cast (CAS number 25971-63-5 base polymer)
Color: Clear
Hardness: Rockwell R 73-78
Temperature Range: −275° F. to 250° F.
Melt point 300° F.+/−5° F.
Length: ⅝"+/−0.010"
Width: ³⁄₁₆"+/−0.010"
Thickness: ⅛"+/−0.010"
Wall Thickness: ¹⁄₁₂₈"+/−0.003"

Another prototype self-contained test was prepared and tested. This prototype self-contained test is described as follows.

Design Decisions Include:
Design may calls for a self-contained strep A test kit composed of a clear tube, red plastic cap red plastic test strip holder, reagent cartridge, test strip, and swab.
Considerations Can Include:
1. Able to be sterilized or disinfected
2. Non-reactive with reagents (acetic acid and sodium nitrate) and test strip (sodium azide)
3. Non-reactive with human tissue
4. Made of FDA approved materials
5. Target manufacturing price is $10 per unit
6. Hydrophobic
Plastic Material Choices Include:
1. Glass
2. Polyethylene (PE)
3. Polyethylene Terephthalate (PET)
4. Acetate
5. Polycarbonate (PC)
6. Polypropylene (PP)
7. Polyvinylchloride (PVC)
8. Acrylic
9. Polyurethane
10. Polylactile acid resin (PLA)
11. Acrylonitrile butadiene styrene (ABS)
12. Nylon The use of polycarbonate, polyvinylchloride, or acrylic for the clear parts and polyvinylchloride or polypropylene for the colored parts may be preferred. These materials are often inexpensive, FDA approved, and non-reactive.

The blister packs, e.g., blister packs 118, 120, may be made of polycarbonate. These blister packs can be made to any size and can be broken open with a sharp impact but are otherwise difficult to accidentally break open.

In many embodiments, test devices described herein may be used for a PCR test. There may be three basic steps to a successful PCR test: specimen collection, specimen processing, and precipitate collection. For many test devices described herein, the specimen collection process may be left to the user and precipitate collection may be accomplished using a simple absorbing test strip. The standard specimen processing procedure can comprise mixing the reagents, swirling the swab in the reagents, squeegeeing the liquid out of the swab, and applying the test strip to the recovered liquid. In many embodiments, swirling the swab is not a necessary step. In many embodiments, squeegeeing the swab can be a vital step to recover the mixed reagent/sample solution from the swab.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments. While the embodiments may be illustrated by using a particular embodiment, this is not and does not limit the invention to any particular embodiment and a person of ordinary skill in the art will recognize that additional embodiments are readily understandable and are a part of the example embodiments.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A self-contained device for determining the presence of an analyte, the device comprising:
   a testing chamber comprising an open portion at or near a first end, a reagent mixing portion at or near a second end opposite the first end, and a wall extending from the open portion to the reagent mixing portion;
   an articulable element coupled to the testing chamber, wherein the articulable element can be articulated to cause a plurality of reagents held by the testing chamber to mix in the reagent mixing portion;
   a cover operably coupled to the open portion of the testing chamber and configured to allow advancement of a specimen into the reagent mixing portion of the testing chamber and close off the open portion; and
   a movable test strip located outside the wall of the testing chamber and configured to be actuated by a mechanism coupled to the testing chamber and the movable test strip, wherein actuation by the mechanism is configured to cause the movable test strip to be advanced outside the wall of the testing chamber into the reagent mixing portion of the testing chamber to determine the presence of an analyte in a mixture of the plurality of reagents and the specimen, wherein the determination comprises a visual change on the movable test strip that is read in the self-contained device.

2. The device of claim 1, wherein the plurality of reagents are held by at least a first reagent storage element and a second reagent storage element, the first reagent storage element comprising a first reagent and the second reagent storage element comprising a second reagent.

3. The device of claim 2, wherein the first reagent storage element comprises a first blister pack and the second reagent storage element comprises a second blister pack.

4. The device of claim 3, wherein articulating the articulable element comprises breaking one or more of the first blister pack and the second blister pack.

5. The device of claim 4, wherein the articulable element comprises one or more projections for tearing or breaking one or more of the first blister pack and the second blister pack.

6. The device of claim 1, wherein the articulable element comprises a pressable button.

7. The device of claim 1, further comprising an elongate specimen collection element having a first end for coupling the elongate element to the cover and a second end opposite the first end for carrying the specimen.

8. The device of claim 7, wherein the cover comprises a depressible button configured to be pressed to advance the second end of the elongate element including the specimen into the reagent mixing portion of the testing chamber.

9. The device of claim 1, further comprising a sliding mechanism coupled to the testing chamber and the test strip, wherein the sliding mechanism is configured to be actuated to advance the test strip into the reagent mixing portion of the testing chamber.

10. The device of claim 1, wherein the test strip is configured to detect the presence of an infectious disease.

11. The device of claim 10, wherein the infectious disease comprises one or more of strep throat, influenza, whooping cough, a sexually transmitted disease, Chlamydia, or Gonorrhea.

12. A method for determining the presence of an analyte with a self-contained device, the method comprising:
    advancing a specimen collection element carrying a specimen thereon from an open portion into a reagent mixing portion of a testing chamber of the self-contained device, wherein the testing chamber comprises a wall extending from the open portion to the reagent mixing portion;
    articulating an articulable element of the self-contained device, thereby causing a first reagent and a second reagent held by the testing chamber to mix in the reagent mixing portion;
    actuating and advancing a movable test strip outside the wall of the testing chamber into the reagent mixing portion of the testing chamber with aid of a mechanism coupled to the testing chamber and the movable test strip; and
    observing the movable test strip in the self-contained device to determine the presence of the analyte in a mixed sample comprising the first reagent, the second reagent, and the specimen.

13. The method of claim 12, wherein mixing the first reagent with the second reagent comprises articulating an articulable element coupled to the testing chamber to open a first reagent storage element and a second reagent storage element to one another.

14. The method of claim 12, wherein advancing the specimen collection element comprises pressing a button of a cover coupled to the testing chamber and the specimen collection element.

15. The method of claim 12, wherein advancing the test strip into the reagent portion of the testing chamber comprises sliding a sliding mechanism coupled to the testing chamber and test strip.

16. The method of claim 12, wherein the test strip is observed to determine the presence of the analyte in the mixed sample to determine the presence of a disease.

17. The method of claim 16, wherein the disease is an infectious disease.

18. The method of claim 17, wherein the infectious disease comprises one or more of strep throat, influenza, whooping cough, a sexually transmitted disease, Chlamydia, and Gonorrhea.

19. The device of claim 1, further comprising a specimen extraction element configured to extract the specimen after it has been mixed with the plurality of reagents.

20. The device of claim 19, wherein the specimen extraction element is a squeegee element configured to squeeze the specimen.

21. The device of claim 19, wherein the specimen extraction element is actuated by the articulable element.

* * * * *